(12) United States Patent
Drmosh et al.

(10) Patent No.: US 12,306,163 B2
(45) Date of Patent: May 20, 2025

(54) METHOD FOR FABRICATING A GAS SENSOR WITH A METAL OXIDE THIN FILM

(71) Applicant: KING FAHD UNIVERSITY OF PETROLEUM AND MINERALS, Dhahran (SA)

(72) Inventors: Qasem Ahmed Drmosh, Dhahran (SA); Zain Hassan Yamani, Dhahran (SA); Mohammad Kamal Hossain, Dhahran (SA)

(73) Assignee: KING FAHD UNIVERSITY OF PETROLEUM AND MINERALS, Dhahran (SA)

( * ) Notice: Subject to any disclaimer, the term of this patent is extended or adjusted under 35 U.S.C. 154(b) by 438 days.

(21) Appl. No.: 17/976,466

(22) Filed: Oct. 28, 2022

(65) Prior Publication Data
US 2023/0070856 A1    Mar. 9, 2023

Related U.S. Application Data

(62) Division of application No. 16/667,258, filed on Oct. 29, 2019, now Pat. No. 11,493,493, which is a division of application No. 15/863,823, filed on Jan. 5, 2018, now Pat. No. 11,525,818.

(51) Int. Cl.
| | |
|---|---|
| *G01N 33/00* | (2006.01) |
| *C23C 8/16* | (2006.01) |
| *G01N 27/12* | (2006.01) |
| *G01N 27/407* | (2006.01) |

(52) U.S. Cl.
CPC ............ *G01N 33/005* (2013.01); *C23C 8/16* (2013.01); *G01N 27/127* (2013.01); *G01N 27/4075* (2013.01)

(58) Field of Classification Search
CPC ............... G01N 33/005; G01N 27/127; G01N 27/4075; C23C 8/16
See application file for complete search history.

(56) References Cited

U.S. PATENT DOCUMENTS

| | | |
|---|---|---|
| 7,963,148 B2 | 6/2011 | Liu et al. |
| 8,263,002 B1 | 9/2012 | Chow |
| 9,133,549 B2 | 9/2015 | Kim et al. |

(Continued)

OTHER PUBLICATIONS

Gao et al. Zinc oxide films formed by oxidation of zinc under low partial pressure of oxygen. Materials Letters. 2003; 57, 1435-1440 (Year: 2003).*

(Continued)

*Primary Examiner* — Luan V Van
*Assistant Examiner* — Randall Lee Gamble, Jr.
(74) *Attorney, Agent, or Firm* — Oblon, McClelland, Maier & Neustadt, L.L.P.

(57) ABSTRACT

A hydrogen gas sensor with a substrate and a zinc oxide nanostructured thin film deposited on the substrate, wherein the zinc oxide nanostructured thin film has a lattice structure with a weight ratio of low binding energy $O^{2-}$ ions to medium binding energy oxygen vacancies in a range of 0.1 to 1.0, and a method of fabricating a gas sensor by thermally oxidizing a metal thin film under low oxygen partial pressure. Various combinations of embodiments of the hydrogen gas sensor and the method of fabricating the gas sensor are provided.

10 Claims, 18 Drawing Sheets

(56) References Cited

U.S. PATENT DOCUMENTS 9,285,332 B2     3/2016    Jang et al.
2010/0012919 A1   1/2010    Park et al.

OTHER PUBLICATIONS

Huang et al. Fabrication and gas-sensing properties of hierarchically porous ZnO architectures. Sensors and Actuators B: Chemical . 2011; 155, pp. 126-133 (Year: 2011).*

Leonardi Two-dimensional Zinc Oxide Nanostructures for Gas Sensor Applications. Chemosensors, 2017; 5 (17), pp. 3-28 (Year : 2017).*

Tonezzer H2 Sensing Properties of Two-Dimensional Zinc Oxide Nanostructures. Talanta. 2014; 122, p. 201-208 (Year: 2014).*

A. Dutta, S. Basu, "Modified Metal-Insulator-Metal (M-I-M) Hydrogen Gas Sensors Based on Zinc Oxide", URL: http://link.springer.com/article/10.1007/BF00144644, Journal of Materials Science: Materials in Electronics, vol. 6, Issue 6, 1995, pp. 415-418.

Oleg Lupan, Guangyu Chai, Lee Chow, "Novel hydrogen gas sensor based on single ZnO nanorod", URL: http://www.sciencedirect.com/science/article/pii/S0167931708003183, Microelectronic Engineering, vol. 85, Issue 11, 2008, pp. 2220-2225.

Li et al. "Porous spheres-like ZnO nanostructure as sensitive gas sensors for acetone detection" Materials Letters 100 (2013) 119-123 (Year: 2013).

Qurashi et al. "Ultra-fast Microwave Synthesis of ZnO Nanowires and their Dynamic Response Toward Hydrogen Gas" Nanoscale Res Lett (2009) 4:948-954 (Year: 2009).

Rajan et al. "An Investigation on Electrical and Hydrogen Sensing Characteristics of RF Sputtered ZnO Thin-Film with Palladium Schottky Contacts" IEEE Sensors Journal—Oct. 2016 (Year: 2016).

Guo et al. "Hollow, porous, and yttrium functionalized ZnO nanospheres with enhanced gas-sensing performances" Sensors and Actuators B 178 (2013) 53-62 (Year: 2013).

Mani et al. "A highly selective room temperature ammonia sensor using spray deposited zinc oxide thin film" Sensors and Actuators B 183 (2013) 459-466 (Year: 2013).

Wen et al. "Gas-sensing property of a nitrogen-doped zinc oxide fabricated by combustion synthesis" Sensors and Actuators B 184 (2013) 78-84 (Year: 2013).

Sun et al. "Fabrication of palladium-zinc oxide-reduced graphene oxide hybrid for hydrogen gas detection at low working temperature" J Mater Sci: Mater Electron (2017) 28:1667-1673 (Year: 2016).

* cited by examiner

METHOD FOR FABRICATING A GAS SENSOR WITH A METAL OXIDE THIN FILM

CROSS-REFERENCE TO RELATED APPLICATIONS

The present application is a Divisional of U.S. application Ser. No. 16/667,258, now allowed, having a filing date of Oct. 29, 2019 which is a Divisional of U.S. application Ser. No. 15/863,823, pending, having a filing date of Jan. 5, 2018.

STATEMENT OF FUNDING ACKNOWLEDGEMENT

The funding support provided by the Center of Excellence in in Nanotechnology (CENT) at King Fahd University of Petroleum and Minerals (KFUPM) is gratefully acknowledged.

STATEMENT REGARDING PRIOR DISCLOSURES BY THE INVENTOR OR A JOINT INVENTOR

Q. A. Drmosh et al., *Hydrogen gas sensing performance of low partial oxygen-mediated nanostructured zinc oxide thin film*. Sensors and Actuators B: Chemical, Volume 248, September 2017, Pages 868-877, which is incorporated by reference in its entirety.

BACKGROUND OF THE INVENTION

Technical Field

The present invention relates to a hydrogen gas sensor with a substrate and a zinc oxide nanostructured thin film deposited thereon, and a method of fabricating a gas sensor.

Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

Zinc oxide (ZnO), a wide-band gap material with dominant defects and ample oxygen vacancies, has been identified as an emerging candidate in the detection of different gases. Higher stability, feasibility to doping, non-toxicity, and low fabrication cost have made zinc oxide a popular compound in gas sensing industries. Zinc oxide in various shapes, e.g. nanorods [O. Lupan, V. V. Ursaki, G. Chai, L. Chowa, G. A. Emelchenko, I. M. Tiginyanu, A. N. Gruzintsev, A. N. Redkin, Selective hydrogen gas nanosensor using individual ZnO nanowire with fast response at room temperature, Sensors and Actuators B, 144 (2010) 56-66], nanotubes [S. Park, High-response and selective hydrogen sensing properties of porous ZnO nanotubes, Current Applied Physics, 16 (2016) 1263-1269], nanowires [M. N. Contreras, J. M. Herrera, L. A. Rios, R. G. Gutiérrez, T. A. Zepeda, O. E. Contreras, Single ZnO Nanowire-Based Gas Sensors to Detect Low Concentrations of Hydrogen, Sensors, 16 (2015), 30539-30544], and thin films [N. H. Al-Hardan, M. J. Abdullah, A. A. Aziz, Sensing mechanism of hydrogen gas sensor based on RF-sputtered ZnO thin films, International Journal of Hydrogen Energy, 35 (2010) 4428-4434] have been fabricated and examined for hydrogen sensing. However, ZnO thin films have not been widely used due to the low sensitivity, as well as low response and recovery time [Q. A. Drmosh, Z. H. Yamani, Synthesis, characterization, and hydrogen gas sensing properties of AuNs-catalyzed ZnO sputtered thin films, Applied Surface Science, 375 (2016) 57-64]. One of the most commonly used techniques for fabricating ZnO thin film sensors is through brush coating, wherein the sensing material is brush-coated on the surface of a substrate. Even though this method is a simple method for fabricating ZnO sensors with different morphologies and sizes, it has several shortcomings, for example, the limitations of the method in large-scale production makes the fabricated sensors inappropriate for commercialization, the repeatability of the coating process is a challenging issue, and the compatibility of the fabricated materials with substrates is relatively low. Sputtering techniques offer the advantages of producing high purity sensors with good reproducibility and relatively high compatibility of the sensing materials with the substrates [K. G. Girija, K. Somasundaram, A. Topkar, R. K. Vatsa, Highly selective $H_2S$ gas sensor based on Cu-doped ZnO nanocrystalline films deposited by RF magnetron sputtering of powder target, Journal of Alloys and Compounds, 684 (2016) 15-20]. However, the compact and smooth columnar structure of ZnO films negatively affects the gas sensing performance. Consequently, two approaches were developed to improve the gas sensing performance of ZnO thin films-based sensors prepared by sputtering. The first approach was a traditional method based on metal-doping of ZnO [T. S. Shishiyanu, T. S. Shishiyanu, O. I. Lupan, Sensing characteristics of tin-doped ZnO thin films as $NO_2$ gas sensor, Sensors and Actuators B, 107 (2005) 379-386; H. Gong, J. Q. Hu, J. H. Wang, C. H. Ong, F. R. Zhu, Nano-crystalline Cu-doped ZnO thin film gas sensor for CO, Sensors and Actuators B, 115 (2006) 247-251; P. P. Sahay, R. K. Nath, Al-doped ZnO thin films as methanol sensors, Sensors and Actuators B, 134 (2008) 654-659]. Energy-band and morphology of the zinc oxide thin films can be modified with this approach. Also, the adsorption area of the zinc oxide thin films can be enhanced thus creating more centers for gas interaction on ZnO surfaces [David C. Pugh, Vandn Luthra, Anita Singh and Ivan P. Parkin, Enhanced gas sensing performance of indium doped zinc oxide nanopowders, RSC Adv., 5 (2015) 85767-85774]. However, doping is generally achieved through a long and complicated preparation process. According to the second approach, a nanostructured ZnO thin film is fabricated via decoration of the nanostructured ZnO surface by noble metals, such as palladium [T. Rashid, D. Phan, G. Chung, Effect of Ga-modified layer on flexible hydrogen sensor using ZnO nanorods decorated by Pd catalysts, Sensors and Actuators B, 193 (2014) 869-876], platinum [Q. A. Drmosh, Z. H. Yamani, Hydrogen sensing properties of sputtered ZnO films decorated with Pt nanoparticles, Ceramics International, 42 (2016) 12378-12384], silver [A. S. M. Iftekhar Uddin, D. Phan, G. Chung, Low temperature acetylene gas sensor based on Ag nanoparticles-loaded ZnO-reduced graphene oxide hybrid, Sensors and Actuators B, 207 (2015) 362-369], and gold [Y. Lin, W. Wei, Y. Wang, J. Zhou, D. Sun, X. Zhang, S. Ruan, Highly stabilized and rapid sensing acetone sensor based on Au nanoparticle-decorated flower-like ZnO microstructures, Journal of Alloys and Compounds, 650 (2015) 37-44]. However, the second approach generally requires complex and time-consuming chemical synthesis routes that increase the cost of the sensing device, and can affect the purity of the sensor.

Recent efforts have been dedicated towards enhancement of gas sensing performance of thin films by oxidation of metallic films in different environments. For instance, Elahi et al [R. Alipour, M. T. Hosseinnejad, A. Salar Elahi, M. Ghorannevis, New perspective on morphological features of the zinc oxide thin films as a gas sensor, Journal of Alloys and Compounds, 687 (2016) 72-78] fabricated ZnO films by thermal oxidation of sputtered Zn films in air and investigated the effect of thermal oxidation time on the morphological properties as well as the gas sensing performance. Azad et al. suggested a method to enhance the performance of a carbon monoxide gas sensor by thermal oxidation of metallic tungsten [A. M. Azad, M. Hammoud, Fine-tuning of ceramic-based chemical sensors via novel microstructural modification Part II: Low level CO sensing by tungsten oxide, $WO_3$, Sensors and Actuators B, 119 (2006) 384-39] and molybdenum [A. M. Azad, Fine-tuning of ceramic-based chemical sensors via novel microstructural modification Part II: Low level CO sensing by molybdenum oxide, $MoO_3$, Sensors and Actuators B, 120 (2006) 25-34] thick films in the presence of a buffer gas mixture of CO and $CO_2$ under low oxygen partial pressure. The results revealed that formation of thick films in the presence of the buffer gas mixture improves the gas sensing performance.

In view of the forgoing, one objective of the present disclosure is to provide a hydrogen gas sensor with a substrate and a zinc oxide nanostructured thin film deposited on the substrate, preferably wherein the zinc oxide nanostructured thin film has a lattice structure with a weight ratio of low binding energy $O^{2-}$ ions to medium binding energy oxygen vacancies in a range of 0.1 to 1.0. Another objective of the present disclosure relates to a method of fabricating a gas sensor by thermally oxidizing a metal thin film under low oxygen partial pressure, which is provided by a gaseous mixture of hydrogen and water vapor.

BRIEF SUMMARY OF THE INVENTION

According to a first aspect, the present disclosure relates to a hydrogen gas sensor, including i) a substrate, ii) a zinc oxide nanostructured thin film deposited on the substrate, wherein the zinc oxide nanostructured thin film has a lattice structure with a weight ratio of low binding energy $O^{2-}$ ions to medium binding energy oxygen vacancies in a range of 0.1 to 1.0.

In one embodiment, the zinc oxide nanostructured thin film is porous with an average pore size of 1 to 20 nm.

In one embodiment, the zinc oxide nanostructured thin film does not contain platinum, palladium, nickel, cobalt, copper, or aluminum.

In one embodiment, the zinc oxide nanostructured thin film has a thickness in the range of 10 to 1,000 nm.

In one embodiment, the substrate is a glass substrate or a silicon wafer substrate.

According to a second aspect, the present disclosure relates to a method of fabricating a gas sensor that comprises a metal oxide nanostructured thin film deposited on a substrate, the method involving i) depositing a metal thin film on the substrate, ii) thermally oxidizing the metal thin film at a temperature of 200 to 1,000° C. in the presence of a gaseous mixture with an oxygen partial pressure in the range of $10^{-60}$ to $10^{-1}$ atm to form the metal oxide nanostructured thin film on the substrate, thereby fabricating the gas sensor.

In one embodiment, the metal oxide nanostructured thin film comprises at least one metal oxide selected from the group consisting of zinc oxide, tin oxide, tungsten oxide, cobalt oxide, niobium oxide, indium oxide, iron oxide, titanium oxide, and gallium oxide.

In one embodiment, the metal oxide nanostructured thin film is a zinc oxide nanostructured thin film, wherein the gas sensor is a hydrogen gas sensor.

In one embodiment, a temperature of the gaseous mixture is in the range of 10 to 100° C. before the thermally oxidizing.

In one embodiment, a temperature of the gaseous mixture is in the range of 80 to 100° C. before the thermally oxidizing, wherein the zinc oxide nanostructured thin film has a sheet-like morphology.

In one embodiment, the gaseous mixture includes hydrogen gas and water vapor, wherein a ratio of a partial pressure of hydrogen gas to a partial pressure of water vapor in the gaseous mixture is in the range of 1:100 to 1:2000, and wherein the gaseous mixture has an oxygen partial pressure in the range of $10^{-20}$ to $10^{-15}$ atm.

In one embodiment, the metal thin film is thermally oxidized in the presence of the gaseous mixture for 2 to 6 hours.

According to a third aspect, the present disclosure relates to a method of determining a concentration of hydrogen gas in a fluid stream, the method involving i) contacting the fluid stream with the hydrogen gas sensor, ii) measuring a response factor, which is a change in an electrical resistance across the zinc oxide nanostructured thin film during the contacting relative to prior to the contacting, iii) determining the concentration of hydrogen gas in the fluid stream based on the response factor.

In one embodiment, the fluid stream has a temperature of 20 to 750° C. during the contacting.

In one embodiment, the concentration of hydrogen gas in the fluid stream is in the range of 50 to 1,500 ppm, wherein the response factor is in the range of 10% to 40%.

In one embodiment, the method has a response time of 0.5 to 6 minutes.

In one embodiment, the fluid stream includes hydrogen gas and at least one of ammonia, butane, pentane, butene, pentene, and carbon dioxide, wherein a hydrogen selectivity of the hydrogen gas sensor is at least 80% by mole.

In one embodiment, the method has a repeatability of at least 99%.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION OF THE EMBODIMENTS

Figure 1:
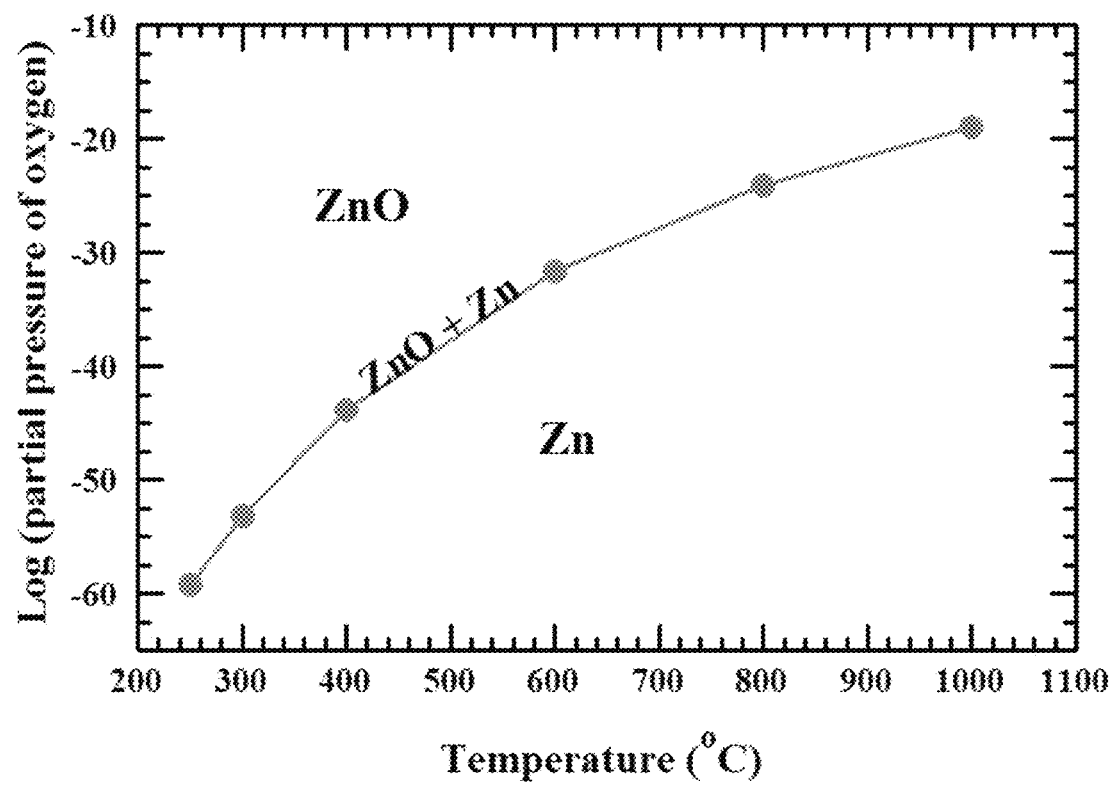
FIG. 1 represents a phase diagram of zinc/zinc oxide.

Referring now to the drawings, wherein like reference numerals designate identical or corresponding parts throughout the several views.

According to a first aspect, the present disclosure relates to a hydrogen gas sensor 200. The term "hydrogen gas sensor" as used in this disclosure refers to a gas sensor for detecting hydrogen gas and/or determining a concentration of hydrogen gas in a fluid stream. The hydrogen gas sensor 200 has a substrate 220 and a zinc oxide nanostructured thin film 222 deposited thereon, wherein an electrical resistance (or an electrical conductance) of the zinc oxide nanostructured thin film 222 varies when the hydrogen gas sensor 200 is subjected (exposed) to a fluid stream having hydrogen gas, due to adsorption of hydrogen gas molecules onto a surface of the zinc oxide nanostructured thin film 222. In view of that, the hydrogen gas sensor may also be referred to as a "chemiresistive hydrogen gas sensor", and these terms may be used interchangeably throughout this disclosure. By detecting the extent of variations of the electrical resistance, a concentration of hydrogen gas in the fluid stream may be determined. FIGS. 2B, 2C, 2D, and 2E schematically represent the hydrogen gas sensor 200 with the substrate 220 and the zinc oxide nanostructured thin film 222 deposited thereon. In some alternative embodiments, a metal oxide nanostructured thin film may be utilized in the hydrogen gas sensor 200 in lieu of the zinc oxide nanostructured thin film 222, wherein the metal oxide nanostructured thin film contains one or more of tin, indium, tungsten, cobalt, niobium, titanium, iron, and gallium.

As used herein, the "substrate" is utilized to support the zinc oxide nanostructured thin film 222. The substrate 220 may be a glass substrate, a sapphire substrate, a quartz substrate, a magnesium oxide single crystal substrate, a ceramic substrate, an alumina substrate, a silicon substrate (e.g. silicon wafer or silicon oxide), a silicon nitride substrate, etc. The substrate 220 may have a thickness of 0.05-10 mm, preferably 0.1-5 mm, preferably 0.2-3 mm, although the thickness of the substrate 220 is not limited to these ranges and substrates with thicknesses outside of these ranges may also be used.

The zinc oxide nanostructured thin film 222 is porous with a plurality of oxygen vacancies that are formed after thermal oxidation of a zinc thin film under low oxygen partial pressures, i.e. at an oxygen partial pressure in the range of $10^{-60}$ to $10^{-1}$ atm, preferably $10^{-40}$ to $10^{-10}$ atm, preferably $10^{-20}$ to $10^{-15}$ atm, and at an oxidation temperature in the range of 200 to 1000° C., preferably 300 to 900° C., preferably 400 to 800° C. In one embodiment, an average pore size of the zinc oxide nanostructured thin film 222 is in the range of 1 to 20 nm, preferably 2 to 18 nm. Accordingly, the "nanostructured" as used in the term "nanostructured thin film" refers to oxygen vacancies present in a thin film. Also, the "thin film" as used in the term "nanostructured thin film" refers to a film with a thickness of no more than 5 μm, preferably in the range of 10 to 1,000 nm. In view of that, the hydrogen gas sensor 200 preferably does not contain thick films of zinc oxide, wherein the term "thick film" refers to a film with a thickness of greater than 5 μm.

The number of oxygen vacancies present in the zinc oxide nanostructured thin film 222 may determine chemiresistive properties, as well as sensitivity, repeatability, and response time of the hydrogen gas sensor 200.

Figure 6A:
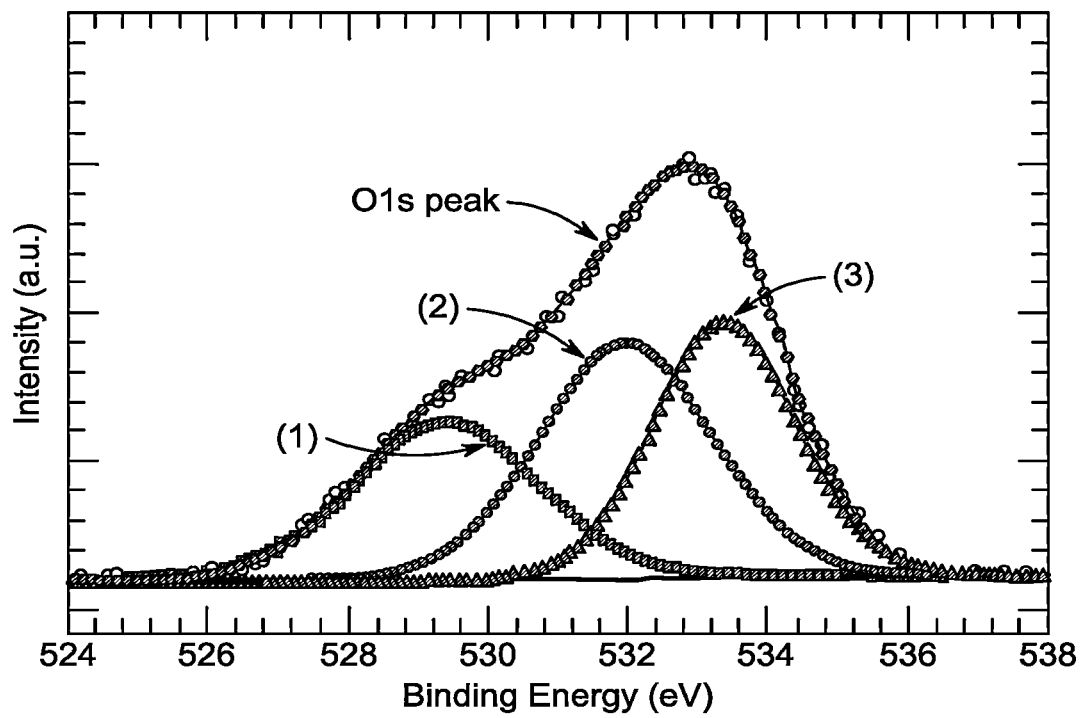
FIG. 6A represents a high resolution XPS spectrum of O1s peak of the zinc oxide nanostructured thin film, which is thermally oxidized at 600° C. under low oxygen partial pressures.

For the hydrogen gas sensor 200, a weight ratio of low binding energy $O^{2-}$ ions (i.e. oxygen in the ZnO lattice) to medium binding energy (i.e. oxygen vacancies) in a lattice structure of the zinc oxide nanostructured thin film 222 (i.e. a wurtzite crystal structure) is in the range of 0.1 to 1.0, preferably 0.4 to 0.9. The weight ratio of low binding energy $O^{2-}$ ions to medium binding energy oxygen vacancies in the lattice structure of the zinc oxide nanostructured thin film 222 may be determined by deconvoluting an O1s peak in an XPS spectrum of the zinc oxide nanostructured thin film 222, as shown in FIG. 6A. Three deconvoluted peaks may be obtained after deconvoluting the O1s peaks of the zinc oxide nanostructured thin film: a first peak (1) relates to $O^{2-}$ ions in the wurtzite ZnO structure at low binding energies; a second peak (2) relates to oxygen vacancies at medium binding energies (MBE); and a third peak (3) relates to OH⁻ or any other surface adsorbed oxygen species at high binding energies (HBE). Accordingly, the weight ratio of low binding energy $O^{2-}$ ions to medium binding energy oxygen vacancies in a lattice structure of the zinc oxide nanostructured thin film 222 may be determined by a peak area ratio of the first peak (1) to the second peak (2), or peak height ratio of the first peak (1) to the second peak (2), as shown in FIG. 6A.

In some embodiments, the zinc oxide nanostructured thin film 222 preferably includes micro-pores (i.e. pores with an average pore diameter of less than 2 nm, preferably in the range of 4-12 Å, more preferably 5-10 Å, even more preferably 6-8 Å) with a micro-pore specific pore volume in the range of 0.01-0.15 cm³/g, preferably 0.02-0.12 cm³/g, more preferably 0.03-0.1 cm³/g, and a micro-pore specific surface area in the range of 10-500 m²/g, preferably 20-400 m²/g, more preferably 30-300 m²/g. The zinc oxide nanostructured thin film may further include meso-pores (i.e. pores with an average pore diameter in the range of 2-50 nm, preferably 5-20 nm) with a meso-pore specific pore volume in the range of 0.1-0.3 cm³/g, preferably 0.15-0.25 cm³/g, and a meso-pore specific surface area in the range of 10-200 m²/g, preferably 20-150 m²/g.

Figure 7:
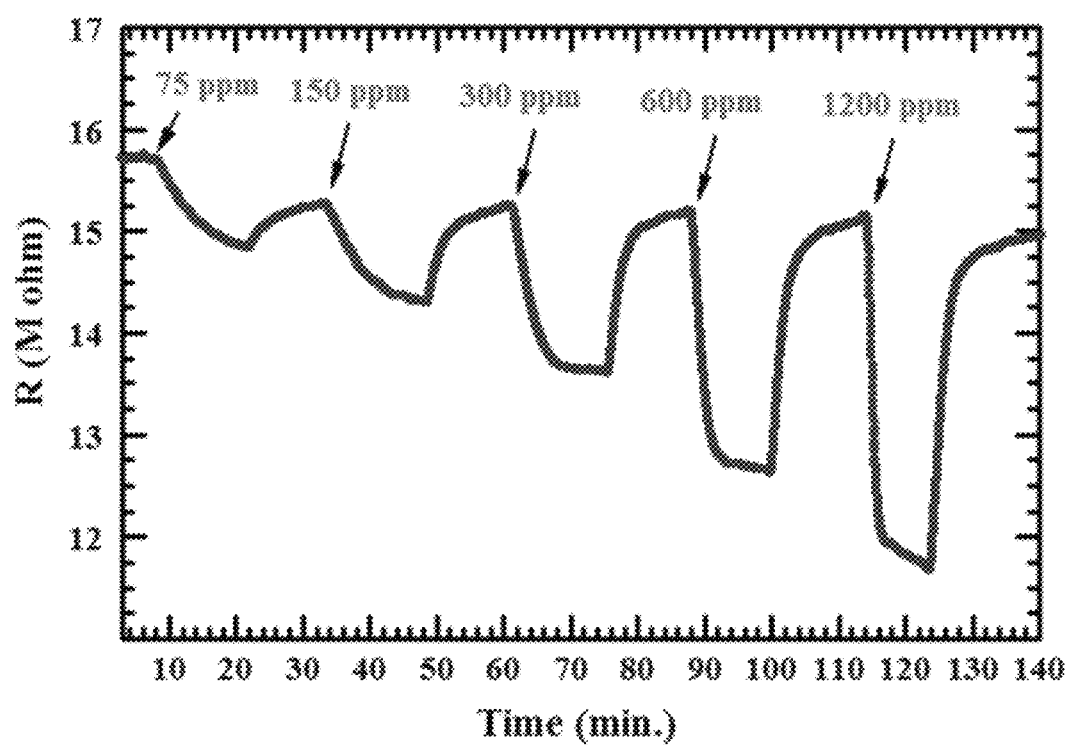
FIG. 7 represents an electrical resistance of the hydrogen gas sensor when consecutively subjected to a fluid stream with different concentrations of hydrogen gas at 400° C., wherein the hydrogen gas sensor is fabricated by thermal oxidation of zinc under low oxygen partial pressures at 600° C.
Figure 8:
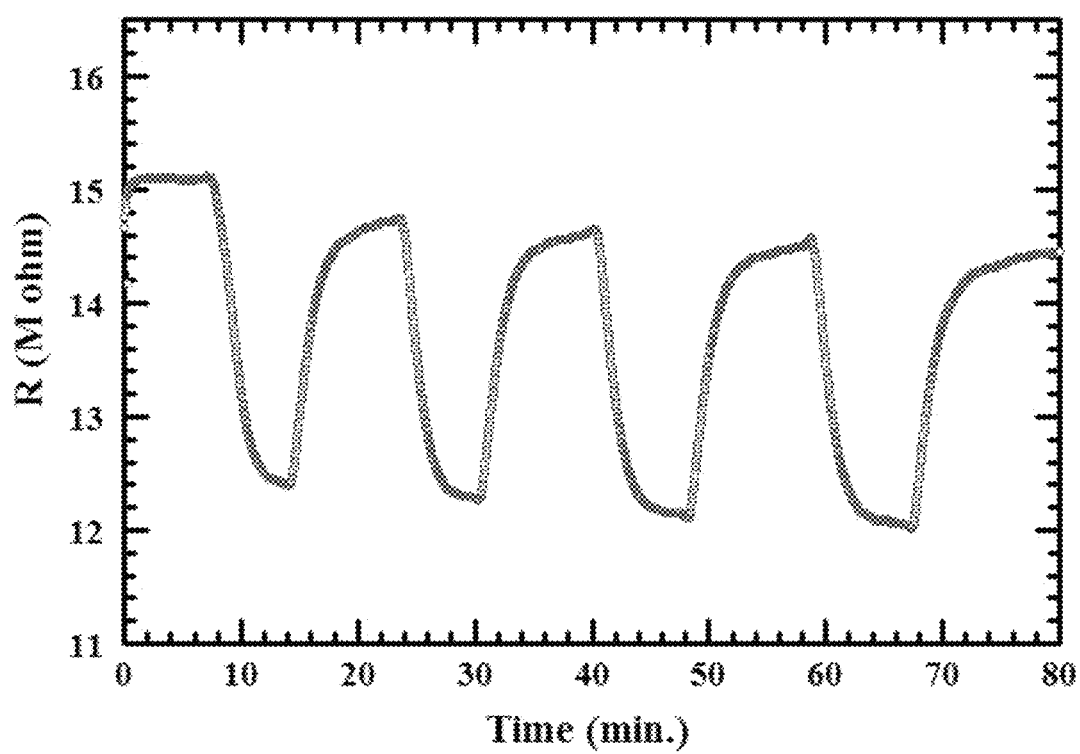
FIG. 8 represents an electrical resistance of the hydrogen gas sensor when consecutively subjected to a fluid stream with a constant concentration of hydrogen gas (600 ppm) at 400° C., wherein the hydrogen gas sensor is fabricated by thermal oxidation of zinc under low oxygen partial pressures at 600° C.

When the zinc oxide nanostructured thin film 222 is contacted with hydrogen gas, the electrical resistance across the zinc oxide nanostructured thin film may drop; while upon removing the hydrogen gas the zinc oxide nanostructured thin film retains an initial electrical resistance. Therefore, a fluctuation in the electrical resistance, and subsequently the response factor, may be identified upon consecutively subjecting the gas sensor to a fluid stream that contains hydrogen gas, as shown in FIGS. 7 and 8. The decrease/increase in the electrical resistance of the zinc oxide nanostructured thin film in the presence/absence of hydrogen gas may be explained as follows: when the zinc oxide nanostructured thin film is exposed to air, the oxygen molecules that are adsorbed onto the zinc oxide nanostructured thin film may capture electrons from a conduction band of the zinc oxide nanostructured thin film. As a result, oxygen ions may form (i.e. $O_2^-$ at a temperature of 20 to 40° C., $O^-$ at a temperature of 100 and 300° C., and $O^{2-}$ at a temperature above 300° C.). Therefore, an electron density of the conduction band of the zinc oxide nanostructured thin film is reduced, and a space charge region, which can serve as a barrier for electron transfer, may be formed on a surface of the zinc oxide nanostructured thin film, thereby causing a high electrical resistance in the zinc oxide nanostructured thin film when exposed to air. When the zinc oxide nanostructured thin film is exposed to hydrogen gas (or any fluid stream containing hydrogen gas), the oxygen ions present on the surface of the zinc oxide nanostructured thin film are desorbed, and the electrons are returned to the conduction band of the zinc oxide nanostructured thin film, thereby leading to a decrease of the electrical resistance of the zinc oxide nanostructured thin film in hydrogen gas.

The hydrogen gas sensor 200 may further be utilized to detect and/or determine a concentration of other gaseous compounds that affect the electrical resistance of the of the zinc oxide nanostructured thin film 222. Exemplary of such gaseous compounds without limitations may include carbon monoxide, nitrogen monoxide, nitrogen dioxide, methane, ethane, methanol, ethanol, hydrogen sulfide, etc. In view of that, the hydrogen gas sensors may also be used to detect exhaust gases or toxic gases, for example, in automobile industries and/or in air pollution control systems.

In some embodiments, the zinc oxide nanostructured thin film 222 does not contain platinum, palladium, nickel, copper, or aluminum in elemental form. In some embodiments, the zinc oxide nanostructured thin film 222 does not contain platinum, palladium, nickel, cobalt, copper, or aluminum in a nanoparticle form.

In one embodiment, the zinc oxide nanostructured thin film 222 has a thickness in the range of 10 to 1,000 nm, preferably 20 to 900 nm. In some embodiments, the zinc oxide nanostructured thin film 222 may have a thickness of greater than 1,000 nm but no more than 5 μm, preferably no more than 4 μm.

The hydrogen gas sensor 200 may be manufactured in various sizes and shapes with respect to the applications. For example, in one embodiment, the hydrogen gas sensor 200 has a surface area of less than 1 cm², preferably less than 0.5 cm², wherein the hydrogen gas sensor 200 can be mounted on a mobile device, such as a mobile phone. Alternatively, the hydrogen gas sensor 200 may have a surface area of up to 50 m², preferably up to 20 m², preferably up to 2.0 m² to be utilized in industrial settings. The hydrogen gas sensor 200 may have various shapes, preferably a disc (as shown in FIGS. 2B, 2C, 2D, and 2E), a slab, a hollow cylinder with the zinc oxide nanostructured thin film 222 deposited on an internal surface of the hollow cylinder, a sphere with the zinc oxide nanostructured thin film 222 deposited on an external surface of the sphere, etc.

According to a second aspect, the present disclosure relates to a method of fabricating a gas sensor that includes a metal oxide nanostructured thin film deposited on a substrate.

In terms of the present disclosure, a gas sensor is a device having a metal oxide nanostructured thin film, as a gas sensitive element, i.e. the metal oxide nanostructured thin film, which is deposited on a substrate. When the metal oxide nanostructured thin film adsorbs a particular gas molecule (e.g. hydrogen gas molecule), the electrical resistance of the metal oxide nanostructured thin film varies. By measuring the variations of the electrical resistance, a concentration of that particular gas molecule in a fluid stream may be determined.

In a first step, the method involves depositing a metal thin film on the substrate. The metal thin film may be deposited on the substrate by various methods know to those skilled in the art, for instance, sputtering, e.g. magnetron sputtering, electron beam deposition, chemical vapor deposition, wet deposition, etc.

In some preferred embodiments, the metal thin film is deposited by sputtering. Accordingly, a sputtering chamber is evacuated to a pressure of less than $3.5 \times 10^{-6}$ Torr, preferably less than $3.0 \times 10^{-6}$ Torr. Then, the sputtering chamber is filled with an inert gas, preferably argon with a purity of 99.9% or preferably a purity of 99.999%, wherein the pressure of the sputtering chamber is raised to at least $5.0 \times 10^{-6}$ Torr, preferably at least $5.3 \times 10^{-6}$ Torr, but no more than $6.0 \times 10^{-6}$ Torr. A partial pressure of the inert gas may preferably be maintained in the range of 0.5-10 mTorr, preferably 1-5 mTorr in the sputtering chamber during sputtering. A sputtering power may set to a value in the range of 50 to 500 W, preferably 100 to 400 W. A pure metal sputtering target, e.g. a pure zinc metal in a form of a disc with a diameter of 5 to 10 centimeters, preferably 6 to 9 centimeters may be used as the pure metal sputtering target. Accordingly, metallic nanoparticles may be ejected from the pure metal sputtering target after bombardment by energetic gas ions, e.g. $Ar^+$. With respect to the pure metal sputtering target, the metallic nanoparticles may include, without limitation, zinc, lead, tin, indium, titanium, iron, gold, silver, ruthenium, rhenium, or combinations thereof. Preferably a pure zinc metal may be used as the pure metal sputtering target for fabricating a hydrogen gas sensor. The metallic nanoparticles may have an average particle size of less than 200 nm, preferably less than 100 nm, preferably 5 to 80 nm, preferably 10 to 50 nm, more preferably 20 to 40 nm. The metallic nanoparticles may have similar rounded shapes, or may have various shapes including, without limitation, spherical, elliptical, cubical, hexagonal, pyramidal, conical, and/or irregular shapes. A thickness of the metal thin film after the sputtering may preferably be in the range from about 1 nm to 1 μm, preferably 20 to 900 nm.

The substrate may be acid-washed before depositing the metal thin film. Washing the substrate with an acid, e.g., sulfuric acid and/or nitric acid may form carboxylate groups on the substrate that may stabilize the metallic nanoparticles on the substrate after sputtering, due to the presence of strong interactions between the metallic nanoparticles and carbon atoms that are present in the carboxylate groups. The substrate may be washed with deionized water after acid-washing.

In some alternative embodiments, the metal thin film is deposited by magnetron sputtering, wherein the sputtering chamber is exposed to an electric/magnetic field, and wherein the sputtering chamber is filled with oxygen and argon with a volume ratio of oxygen to argon in the range of 2:1 to 4:1, preferably about 3:1. Alternatively, the sputtering chamber is filled with ambient air. The sputtering power may be set to a value of 400 to 800 W, preferably about 600 W. The substrate may be rotated during the sputtering process.

Sputtering the metal thin film on the substrate may preferably be performed at a temperature of less than 140° C., preferably less than 100° C.

The method may further include patterning the metal thin film using methods known to those skilled in the art, e.g. dry etching or wet etching. Accordingly, the metal thin film may be patterned into an interdigitated electrode (IDE) pattern or other patterns known to those skilled in the art, e.g. a finger (or comb)-shaped pattern, etc.

In a second step, the method involves thermally oxidizing the metal thin film at a predetermined temperature and a predetermined oxygen partial pressure. For each metal, the predetermined temperature and the predetermined oxygen partial pressure may be obtained from a phase diagram that correlates temperatures and oxygen partial pressures, wherein the metal thin film is thermodynamically equilibrates with its corresponding metal oxide. For example, FIG. 1 represents a phase diagram of zinc metal and zinc oxide (Zn/ZnO).

Thermally oxidizing the metal thin film at the predetermined temperature and the predetermined oxygen partial pressure may turn the metal thin film into a metal oxide nanostructured thin film with specific characteristics, e.g. high concentration of oxygen vacancies as described previously. Therefore, the "metal oxide nanostructured thin film" is a porous film with a plurality of oxygen vacancies, and an average pore size of 1 to 50 nm, preferably 2 to 40 nm.

In view of that, in a preferred embodiment, a zinc thin film is oxidized at a pressure of 200 to 1,000° C., preferably 300 to 900° C., preferably 400 to 800° C. in the presence of a gaseous mixture with an oxygen partial pressure in the range of $10^{-60}$ to $10^{-1}$ atm, preferably $10^{-40}$ to $10^{-10}$ atm, preferably $10^{-20}$ to $10^{-15}$ atm, to form the zinc oxide nanostructured thin film on the substrate.

In some embodiments, the metal thin film may include at least one element selected from the group consisting of zinc, tin, indium, tungsten, cobalt, niobium, titanium, iron, and gallium. Accordingly, the metal oxide nanostructured thin film may contain at least one metal oxide selected from the group consisting of zinc oxide, tin oxide, tungsten oxide, cobalt oxide, niobium oxide, indium oxide, iron oxide, titanium oxide, and gallium oxide. In some alternative embodiments, the metal oxide nanostructured thin film may contain at least one metal oxide with an energy band gap of at least 2.7 eV, preferably in the range of 2.7 to 6.5 eV. In the embodiments where more than one metal oxide is present, the metal oxide nanostructured thin film may preferably be in a form of a stacked multilayer film, wherein each layer contains one metal oxide.

According to the method of the present disclosure, elements present in the metal thin film are oxidized after depositing the metal thin film on the substrate, and thus this method does not involve deposition of metal oxide particles.

Figure 2A:
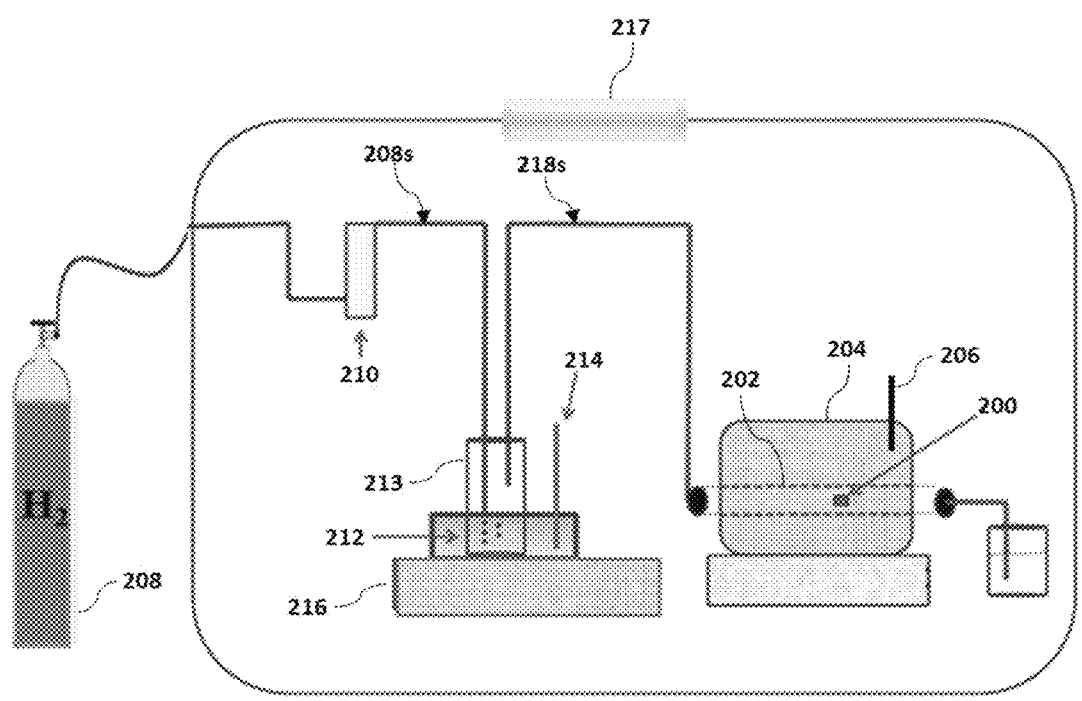
FIG. 2A illustrates a setup for thermal oxidation of a metal thin film deposited on a substrate at low partial pressure of oxygen.
Figure 2B:
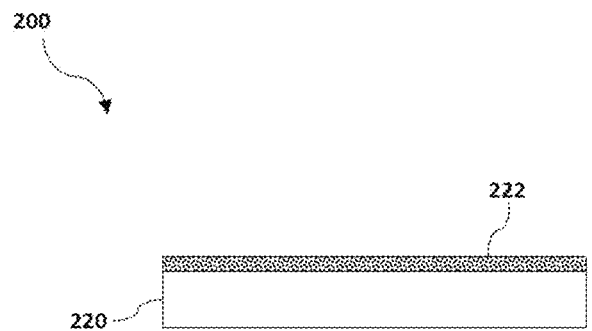
FIG. 2B schematically illustrates a side-view of a hydrogen gas sensor with a substrate and a zinc oxide nanostructured thin film deposited thereon, wherein the zinc oxide nanostructured thin film covers an entire surface area of the substrate.
Figure 2C:
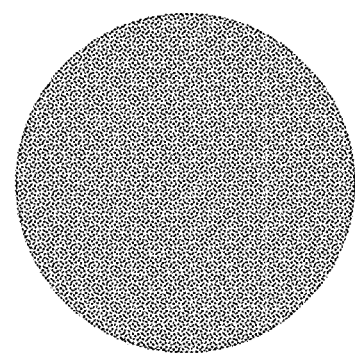
FIG. 2C schematically illustrates a top-view of a hydrogen gas sensor with a substrate and a zinc oxide nanostructured thin film deposited thereon, wherein the zinc oxide nanostructured thin film covers an entire surface area of the substrate.
Figure 2D:
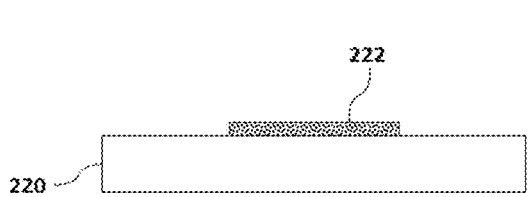
FIG. 2D schematically illustrates a side-view of a hydrogen gas sensor with a substrate and a zinc oxide nanostructured thin film deposited thereon, wherein the zinc oxide nanostructured thin film covers a portion of the surface area of the substrate.
Figure 2E:
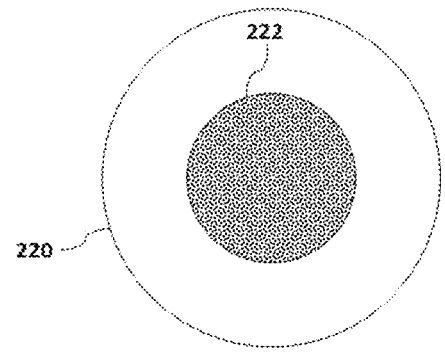
FIG. 2E schematically illustrates a top-view of a hydrogen gas sensor with a substrate and a zinc oxide nanostructured thin film deposited thereon, wherein the zinc oxide nanostructured thin film covers a portion of the surface area of the substrate.

Referring now to FIGS. 2A, 2B, 2C, 2D, and 2E, in some preferred embodiments, a substrate with a zinc thin film deposited thereon is placed in a tube 202, and the tube 202 is further heated in a furnace 204 at a temperature of 200 to 1,000° C., preferably 300 to 900° C., preferably 400 to 800° C., while a gaseous mixture 218s is passed through the tube 202. The gaseous mixture 218s may be prepared by injecting a hydrogen gas stream 208s, which may be supplied from a hydrogen tank 208 with a pressure of 1 to 3 atm or 1 to 1.5 atm, into water 212, preferably deionized water which is maintained at a temperature of 20 to 100° C., preferably 40 to 90° C., preferably 50 to 80° C. The temperature of the water 212 may be raised by any device known to those skilled in the art, e.g. a hot plate 216, as shown in FIG. 2A. Also, the temperature of water 212 may be monitored with the thermometer 214, and the temperature inside the furnace 204 may be monitored with the thermometer 206. In addition, an injection rate of the hydrogen gas stream 208s may be controlled with a flow controller 210. The gaseous mixture 218s is an overhead vapor, which is accumulated in the vessel 213, wherein the gaseous mixture 218s contains hydrogen gas, water vapor, and traces amount of oxygen gas. Partial pressure of each components of the overhead vapor (or the gaseous mixture 218s) can be controlled via the temperature of water 212. A partial pressure of the hydrogen gas and the water vapor may be adjusted with respect to the phase diagram of the metal thin film that is thermally oxidized. When the metal thin film is a zinc thin film, a ratio of the partial pressure of hydrogen gas to the partial pressure of water vapor in the gaseous mixture may preferably be adjusted to be in the range of 1:100 to 1:2,000, preferably 1:500 to 1:1,500, preferably about 1:1,000. Accordingly, an oxygen partial pressure of the gaseous mixture may drop to a value in the range of $10^{-20}$ to $10^{-15}$ atm, preferably $10^{-19}$ to $10^{-16}$ atm, preferably about $10^{-18}$ atm, when the zinc thin film is thermally oxidized at a temperature of 550 to 650° C., preferably about 600° C. As a result, a hydrogen gas sensor 200 is fabricated, which includes the zinc oxide nanostructured thin film 222 deposited on the substrate 220. The zinc oxide nanostructured thin film 222 may cover an entire surface area of the substrate 220, as shown in FIGS. 2B and 2C, or a portion of the surface area (e.g. 30% to 80%, preferably 40% to 70%) of the substrate 220, as shown in FIGS. 2D and 2E. Preferably, the metal thin film (e.g. a zinc thin film) is thermally oxidized in a ventilated area provided by a fume hood 217, or the like.

Preferably, the metal thin film may be thermally oxidized in the presence of the gaseous mixture for 2 to 6 hours, preferably 3 to 5 hours, preferably about 4 hours. Alternatively, the metal thin film may be thermally oxidized for durations that fall outside of these ranges based on the type of the metal thin film.

Figure 3D:
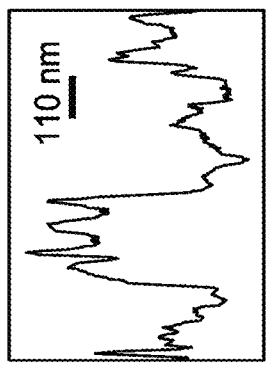
FIG. 3D is a line profile along the dashed line of the surface of the zinc oxide nanostructured thin film of FIG. 3C.
Figure 3H:
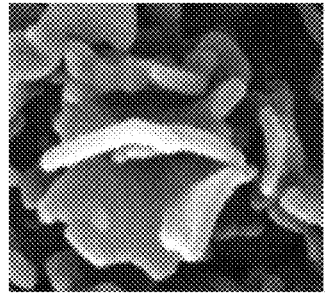
FIG. 3H is a magnified SEM micrograph from a surface of the zinc oxide nanostructured thin film that represents a sheet-like morphology.
Figure 3C:
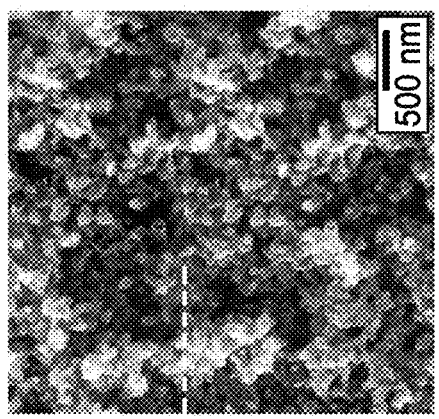
FIG. 3C is a SEM micrograph from a surface of the zinc oxide nanostructured thin film, which is thermally oxidized under low oxygen partial pressures in the presence of a gaseous mixture of hydrogen gas and water vapor, wherein the water vapor is an overhead vapor of water at 40° C.
Figure 3G:
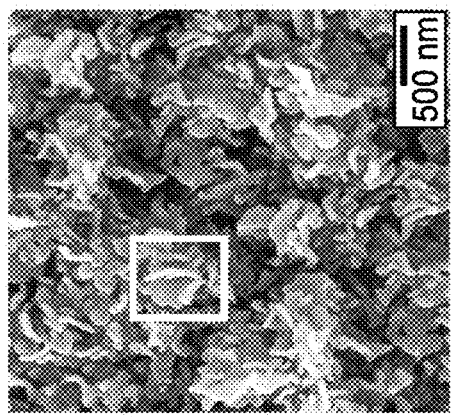
FIG. 3G is a SEM micrograph from a surface of the zinc oxide nanostructured thin film, which is thermally oxidized under low oxygen partial pressures in the presence of a gaseous mixture of hydrogen gas and water vapor, wherein the water vapor is an overhead vapor of water at 80° C.
Figure 3B:
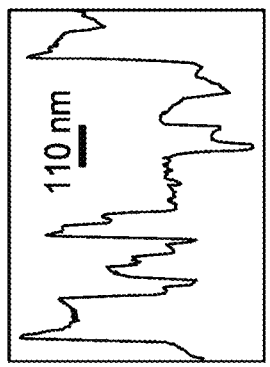
FIG. 3B is a line profile along the dashed line of the surface of the zinc oxide nanostructured thin film of FIG. 3A.
Figure 3F:
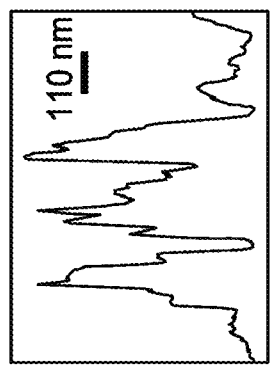
FIG. 3F is a line profile along the dashed line of the surface of the zinc oxide nanostructured thin film of FIG. 3E.
Figure 3A:
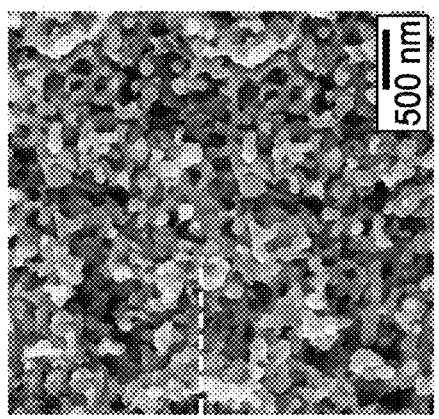
FIG. 3A is a SEM micrograph from a surface of the zinc oxide nanostructured thin film, which is thermally oxidized under low oxygen partial pressures in the presence of a gaseous mixture of hydrogen gas and water vapor, wherein the water vapor is an overhead vapor of water at 20° C.
Figure 3E:
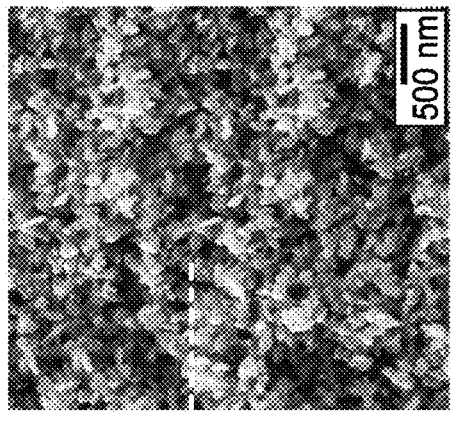
FIG. 3E is a SEM micrograph from a surface of the zinc oxide nanostructured thin film, which is thermally oxidized under low oxygen partial pressures in the presence of a gaseous mixture of hydrogen gas and water vapor, wherein the water vapor is an overhead vapor of water at 60° C.

Since the temperature of water 212 may determine the partial pressure of each components (particularly the oxygen partial pressure) of the gaseous mixture 218s, the temperature of water 212 may determine a concentration of oxygen vacancies and/or morphology of the metal oxide nanostructured thin film (e.g. zinc oxide nanostructured thin film). Preferably, the temperature of water 212 is set to a value in the range of 10 to 100° C., preferably 15 to 80° C., preferably 20 to 60° C. In some embodiments, the temperature of water 212 may affect a surface morphology of the zinc oxide nanostructured thin film. For example, in one embodiment, the temperature of water 212 may be in the range of 80 to 100° C., preferably 80 to 90° C., more preferably about 80° C., wherein the zinc oxide nanostructured thin film has a sheet-like morphology as shown in FIGS. 3G and 3H. Alternatively, in some embodiments the temperature of water 212 may be less than 70° C., or less than 50° C., wherein the zinc oxide nanostructured thin film has a grain-like morphology as shown in FIGS. 3A, 3C, and 3E.

According to a third aspect, the present disclosure relates to a method of determining a concentration of hydrogen (or preferably hydrogen gas) in a fluid stream with the hydrogen gas sensor.

The fluid stream is preferably a gaseous stream that contains hydrogen gas and one or more of water vapor, carbon dioxide, ammonia, butane, pentane, butene, pentene, and so forth. Alternatively, the fluid stream may be a liquid stream, e.g. tap water, seawater, wastewater, or water from a river, a lake, a pond, etc. with infused or dissolved hydrogen. In some embodiments, the fluid stream may be a blood sample. Preferably, the concentration of hydrogen in the fluid stream may be within the range of 50 to 1,500 ppm, preferably 50 to 1,400 ppm. The concentration of hydrogen in the fluid stream is not limited thereto, and the concentration of hydrogen (or hydrogen gas) outside of these preferable ranges can also be determined with the hydrogen gas sensor. For example, in some embodiments, the hydrogen gas sensor may determine the concentration of hydrogen gas of at least 1 ppm, preferably at least 5 ppm, preferably at least 10 ppm. The hydrogen gas sensor may have a detection limit (lowest detectable concentration of hydrogen gas) of 1 to 1,000 ppb, preferably 5 to 500 ppb. The term "detection limit" as used herein, refers to the lowest concentration value detectable by the hydrogen gas sensor.

According to the method, in a first step the fluid stream is contacted with the hydrogen gas sensor (i.e. with the zinc oxide nanostructured thin film of the hydrogen gas sensor). In some embodiments, the fluid stream is a liquid stream, wherein the hydrogen gas sensor is submerged (or partially submerging) therein. In some preferred embodiments, the fluid stream is a gaseous stream, which is passed over the hydrogen gas sensor. Preferably, the fluid stream may have a temperature of 20 to 750° C., preferably 50 to 700° C., preferably 200 to 600° C. during contacting with the hydrogen gas sensor; and therefore, the concentration of hydrogen (or hydrogen gas) in the fluid stream is preferably determined at these preferable temperature ranges.

Once the fluid stream is contacted with the hydrogen gas sensor, the electrical resistance of the zinc oxide nanostructured thin film varies, as described previously. Then, a response factor of the hydrogen gas sensor is measured. The response factor of the hydrogen gas sensor refers to a difference in an electrical resistance across the zinc oxide nanostructured thin film during contacting with the fluid stream relative to prior to the contacting, which may be measured with the following equation (I):

$$\text{Response factor}(\%) = \frac{R_0 - R_g}{R_0} \times 100 \qquad (I)$$

wherein $R_0$ (initial electrical resistance) is the electrical resistance of the hydrogen gas sensor in air, and $R_g$ is the electrical resistance of the hydrogen gas sensor after contacting with the fluid stream. Each of $R_0$ and/or $R_g$ may be independently measured by a device known to those skilled in the art, e.g. an ohm-meter, an avometer, etc.

Once the response factor of a fluid stream is measured, the concentration of hydrogen (or hydrogen gas) may further be determined in the fluid stream based on the response factor. The concentration of hydrogen (or hydrogen gas) may be determined from the response factor via a calibration curve that correlates the response factor to the concentration of hydrogen (or hydrogen gas). For example, in some embodiments, the response factor is non-linearly correlated to the concentration of hydrogen (or hydrogen gas), and the calibration curve may have a general formula as represented by equation (II):

$$[H_2] = A*RF^2 + B*RF + C \qquad (II)$$

wherein "$[H_2]$" represents the concentration of hydrogen (or hydrogen gas) (in ppm), "RF" is the response factor, "A" is a first constant value in the range of 0.001 to 1,000, preferably 0.005 to 900, "B" is a second constant value in the range of 0.001 to 1,000, preferably 0.005 to 900, and "C" is a third constant value in the range of 0.001 to 1,000, preferably 0.005 to 900.

In one embodiment, the concentration of hydrogen gas in the fluid stream is in the range of 0.1 to 1,500 ppm, preferably 60 to 1,400 ppm, preferably 70 to 1,300 ppm, wherein the response factor is in the range of 10% to 60%, preferably 12% to 55%.

Figure 12:
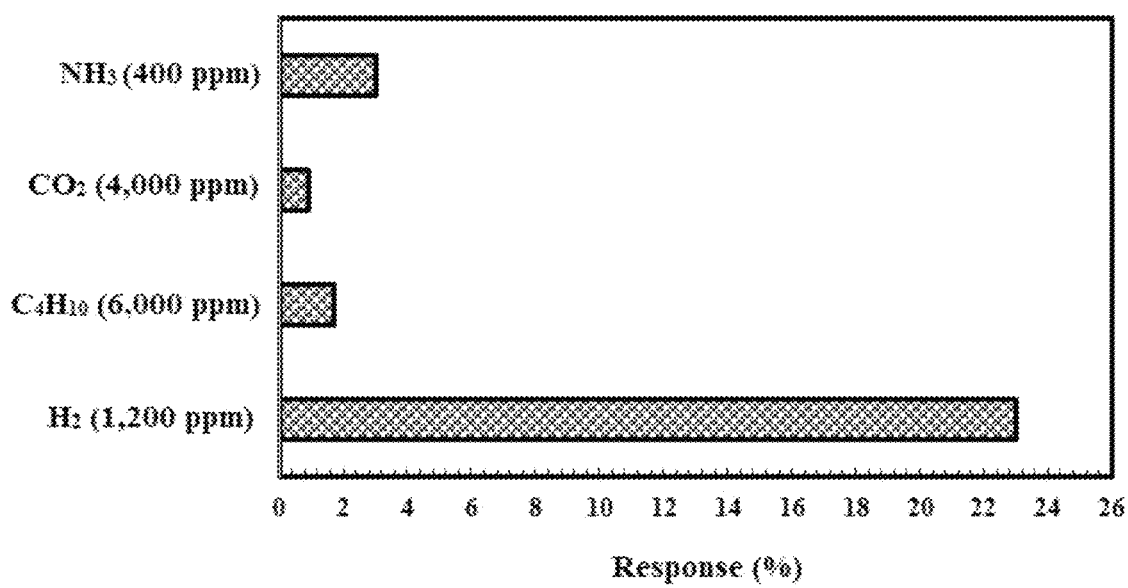
FIG. 12 represents values of the response factor of the hydrogen gas sensor when separately subjected to a fluid stream that contains ammonia; carbon dioxide; butane; and hydrogen gas, at 400° C., wherein the hydrogen gas sensor is fabricated by thermal oxidation of zinc under low oxygen partial pressures at 600° C.

In one embodiment, the fluid stream is a gaseous stream that includes hydrogen gas and at least one compound selected from the group consisting of ammonia, butane, pentane, butene, pentene, and carbon dioxide, wherein a hydrogen selectivity of the hydrogen gas sensor is at least 80% by mole. As used herein, the term "hydrogen selectivity" refers to a ratio of a number of moles of the hydrogen gas that are adsorbed onto the zinc oxide nanostructured thin film relative to the total number of moles that are adsorbed onto the zinc oxide nanostructured thin film. For example, the hydrogen selectivity of the 80% by mole refers to an embodiment wherein 80% of all species that are adsorbed onto the zinc oxide nanostructured thin film is hydrogen. The hydrogen selectivity of the hydrogen gas sensor 200 may be related to the specific surface area and the concentration of oxygen vacancies of the zinc oxide nanostructured thin film. The hydrogen selectivity of the hydrogen gas sensor 200 for a fluid stream that includes ammonia, butane, and carbon dioxide is shown in FIG. 12.

Figure 11:
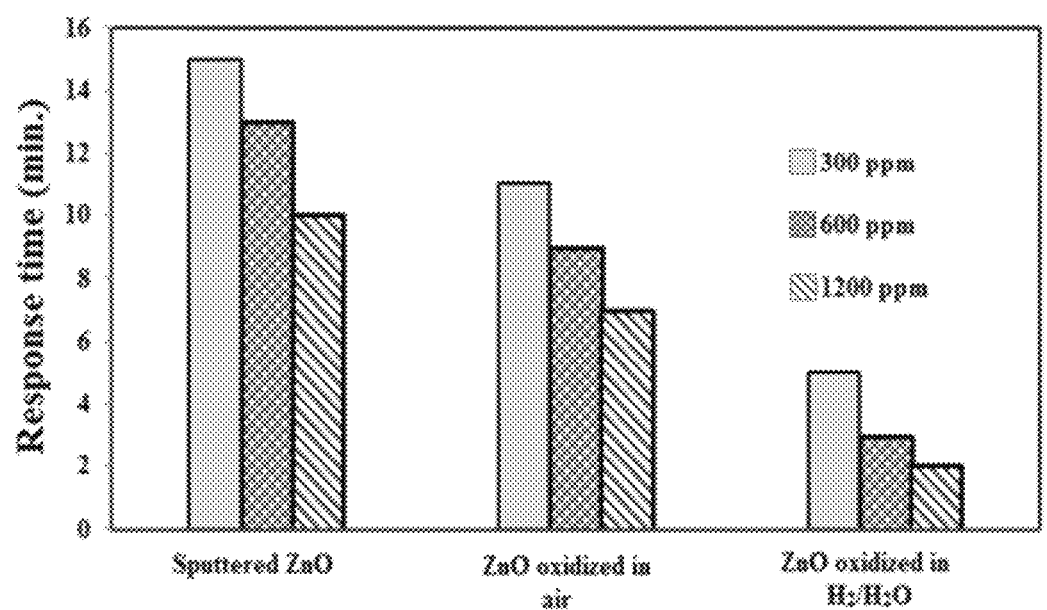
FIG. 11 represents values of the response time of the hydrogen gas sensor when subjected to a fluid stream with different concentrations of hydrogen gas at 400° C., wherein the hydrogen gas sensor is fabricated by DC reactive sputtering followed by thermal oxidation in argon at 600° C.; by thermal oxidation of zinc in air at 600° C.; and by thermal oxidation of zinc under low oxygen partial pressures at 600° C.

In some embodiments, the method has a response time in the range of 0.1 to 6 minutes, as shown in FIG. 11. The term "response time" as used in this disclosure is the amount of time during which the electrical resistance of the hydrogen gas sensor is reduced by 90% relative to an initial electrical resistance. The response time of determining the concentration of hydrogen in a fluid stream may depend on the concentration of hydrogen in the fluid stream. For example, the response time may be around 4 to 6 minutes, preferably about 5 minutes, for a fluid stream with a concentration in the range of 200 to 500 ppm, preferably about 300 ppm; whereas the response time may be in the range of 1 to 3 minutes, preferably about 2 minutes, for a fluid stream with a concentration in the range of 1,000 to 1,500 ppm, preferably about 1,200 ppm.

In some embodiments, the method has a repeatability of at least 99%, preferably at least 99.5%. The term "repeatability" as used herein refers to a relative difference between a first hydrogen concentration measurement and a second hydrogen concentration measurement, wherein the first and the second hydrogen concentration measurements are conducted at substantially the same conditions (i.e. temperature, pressure, composition of the fluid stream, etc.).

Preferably, the hydrogen gas sensor does not substantially age over time. The term "age" as used herein refers to degradation in properties of the hydrogen gas sensor over an extended period of time, e.g., at least two year, preferably more than two years. These properties may include detection limit, response time, repeatability, etc. For example, in some preferred embodiments, the hydrogen gas sensor is maintained for at least two years, preferably at least three years (for example at room temperature, i.e. 20 to 25° C., and atmospheric pressures, i.e. around 1 atm, in an inert atmosphere, e.g. argon), wherein a repeatability of determining the concentration of hydrogen gas using the hydrogen gas sensor is at least 99%, preferably at least 99.5%.

The examples below are intended to further illustrate protocols for the hydrogen gas sensor and methods of fabricating and using thereof, and are not intended to limit the scope of the claims.

EXAMPLE 1

The thermodynamics factors such as surface energy, the Gibbs free energy change, and the enthalpy change are strongly influencing the structure, composition and morphology of the growth of nanostructured ZnO films. The change of the Gibbs free energy ($\Delta G^0$) of the oxidation of Zn to ZnO at well-defined $PO_2$ is given by:

$$\Delta G^0 = -RT\ln(K_1)$$

wherein $$K_1 = \frac{PZnO}{PZnPO_2^{1/2}}$$

where R is the ideal gas constant, T is the absolute temperature, PZn and PZnO are zinc and zinc oxide partial pressure, respectively. Since zinc and zinc oxide are pure solid, it is possible to assume that their partial pressure to be unity and hence oxygen partial pressure can be written as a function of Gibbs free energy change and temperature as:

$$\ln PO_2^{1/2} = \frac{2\Delta G^0}{RT}$$

Gibbs free energy change can be also expressed in terms of the standard Gibbs free energy of formation as follows:

$$\Delta G^0 = \Delta G^0_{f(ZnO)} - \left(\Delta G^0_{f(Zn)} + \frac{1}{2}\Delta G^0_{f(O)}\right)$$

where $\Delta G^0_{f(ZnO)}$, $\Delta G^0_{f(Zn)}$, and $\Delta G^0_{f(O2)}$ are the standard Gibbs free energy of formation of ZnO, Zn and $O_2$ respectively. According to Paul et al. [A. Paul, H. N. Achary, Equilibrium thermodynamics of nonstoichiometry in ZnO and aluminium doping of ZnO using aluminium chloride, Journal of Materials Science, 27 (1992) 1716-1722], by taking into account the followings:

$\Delta G^0_{f(Zn)} = \Delta G^0_{f(O2)} = 0$, and $\Delta G^0_{f(ZnO)} = -84,100 - 6.9T \log T + 44.1T$ one can write the oxygen partial pressure as a function of temperature as follows:

$$\ln PO_2 = \frac{2\Delta G^0_{f(ZnO)}}{RT} = \frac{-84,100 - 6.9T\log T + 44.1T}{RT}$$

This equation gives the theoretical values of thermodynamic equilibrium oxygen partial pressure required for Zn/ZnO coexistence at a given temperature. The data obtained in the range 250-1000° C. is plotted in FIG. 1. If the Zn film is simply heated at oxygen partial pressure above the 'line of Zn/ZnO coexistence', it leads to thermal oxidation of ZnO films whose morphological features may be different from the starting Zn material.

Low $PO_2$ in the vicinity of Zn/ZnO nearness line (solid line in FIG. 1) could be created by manipulating the ratio of $H_2/H_2O$ mixture by virtue of the following equilibrium:

$$H_2 + \frac{1}{2}O_2 \rightarrow H_2O$$

The standard Gibbs energy change ($\Delta G^0_{H2O}$) and the standard Gibbs free energy change for the formation of $H_2O$ [O. Kubaschewski, C. B. Alcock, Metallurgical Thermochemistry 4th edition] is given by:

$$\Delta G^0_{H_2O} = -RT\ln K_2$$

$$\Delta G^0_{H_2O} = -58900 + 13.1T_2$$

wherein $$K_2 = \frac{PH_2O}{PH_2PO_2^{1/2}}$$

Accordingly, the equilibrium oxygen partial pressure produced from the above reaction is given by:

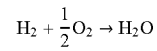

$$PO_2 = \left(\frac{PH_2O}{PH_2}\right)^2 e^{\frac{2(-58900+13.1T_2)}{RT_2}}$$

Therefore, a thermal oxidation in a proper temperature as well as a buffer gas mixture of water vapor, and hydrogen could lead to low values of oxygen partial pressure. For example, if the annealing temperature and the ratio of $H_2O$ to $H_2$ are 600 (i.e. 873 K) and $10^{-3}$, the oxygen partial pressure value will be about $10^{-18}$ atm, which is near the equilibrium Zn/ZnO coexistence as in FIG. 1 and much far away from thermal oxidation in air in which oxygen partial pressure is about 0.21 atm.

EXAMPLE 2—FABRICATING THE SENSOR

The metallic Zn films were fabricated by DC sputtering (NSC4000-Nanomaster) and then transferred for oxidation under controlled parameters in $H_2/H_2O$ mixture at different temperatures. The sputtering chamber was evacuated to a background pressure below $3.5\times10^{-6}$ Torr and then filled with high purity Ar (>99.999%) up to $5.3\times10^{-6}$ Torr. The deposition power was set to be 100 W and the deposition time of 20 min was maintained. FIG. 2A shows the schematic of the experimental setup designed for creating the desired oxygen partial pressure required for oxidation of Zn films. The prepared sputtered Zn film was placed in a tube furnace (OTF-1200X from MTI Corp.) and $H_2$ gas (1 atm) was introduced through a calibrated flow meter to a closed flask containing deionized water. The temperature of the water can be raised to 80° C. Oxygen dissolved in the water reacts with the introduced hydrogen. The water vapor partial pressure on the surface of the water can be calculated using Antoine formula [A. Senol, Solvation-based vapour pressure model for (solvent+salt) systems in conjunction with the Antoine equation, J. Chem. Thermodynamics, 67 (2013) 28-39]. The water partial pressure was controlled by variation the water heating temperature (T*). The Zn thin films were then annealed in the tube furnace at temperature ranging from 400 to 800° C. in $H_2/H_2O$ mixture at different values of oxygen partial pressure for 4 h. All experiments were carried out in the fume hood due to the flammable nature of the gas. The morphological, structural, compositional and gas sensing properties of the prepared samples were compared with ZnO films prepared by DC reactive sputtering, conventional one-step deposition method, and ZnO obtained by the thermal oxidation of sputtered zinc films at atmospheric pressure (oxygen partial pressure=0.21 atm.).

EXAMPLE 3—SENSOR CHARACTERIZATION

The sensing tests of the developed sensors toward hydrogen were performed using sequentially introducing of air and hydrogen balanced nitrogen (1% $H_2$, 99% $N_2$) into the gas sensing chamber called Linkam stage (Model HFS-600E-PB4, UK) that could be used to temperatures up to 600° C. with temperature stability less than 0.1° C. Two mass flow controllers (MFCs) connected with an external X PH-100 power hub supply were utilized to control the flow rate of pure dry air that acts as the carrier gas, and hydrogen balance nitrogen. Prior to introducing hydrogen, the Linkam stage was purged by dried air with a duration time of 50 min under a flow rate of 40 sccm (standard cubic centimeter per minute). The gas sensing response is evaluated by normalized resistance change as follows:

$$\text{Response}(\%) = \frac{R_0 - R_g}{R_0} \times 100$$

where $R_0$ and $R_g$ are the resistances of the sensor in air and analyte gas, respectively calculated via an Agilent B1500A Semiconductor Device Analyzer (SDA). The sensor response was investigated within 75-1200 ppm of hydrogen gas in dry air at a temperature range of (RT-500° C.). The sensing performance of the fabricated materials was systematically evaluated by studying three important sensing characteristics: (I) response to $H_2$ gas, (II) response time, and (III) sensor reproducibility over repeated cycles.

EXAMPLE 4—MORPHOLOGICAL CHARACTERIZATION OF THE THIN FILM LAYER

The morphology of the prepared films was observed via Field Emission Scanning Electron Microscopy (FESEM). The images were obtained using Tuscan microscope equipped with secondary detector and backscattering detector operating at 20 kV.

It was clearly observed that low oxygen partial pressure did have great impact on ZnO film morphology as shown in FIGS. 3A, 3C, 3E, and 3G. These SEM micrographs represent a typical ZnO films that is grown at various oxygen partial pressure modified by applied temperatures (T*) of 20° C., 40° C., 60° C. and 80° C., respectively. At low temperature, such as 20° C., grains were found to be larger along with higher porosity as shown in FIG. 3A. The height profile along a while dotted line marked therein has been included as inset. At increasing temperatures, such as 40° C. and 60° C., the gains sizes were observed to be smaller as shown in FIG. 3C and FIG. 3E. The height profiles along while dotted lines marked therein have been included as insets at temperature such as 80° C., ZnO gains were found to turn into elongated and leaf-like shape which in fact increases open surface of ZnO nanostructures. A typical high resolution image has been included as an inset in FIG. 3G (i.e. FIG. 3H).

Figure 4A:
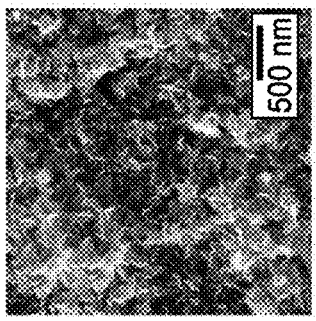
FIG. 4A is a SEM micrograph from a surface of the zinc oxide nanostructured thin film, which is thermally oxidized at 400° C. and under low oxygen partial pressures in the presence of a gaseous mixture of hydrogen gas and water vapor, wherein the water vapor is an overhead vapor of water at 20° C.
Figure 4B:
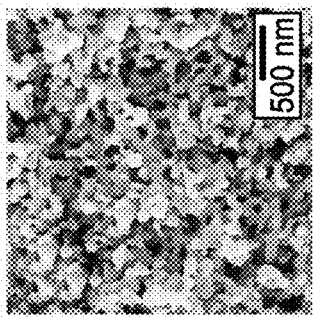
FIG. 4B is a SEM micrograph from a surface of the zinc oxide nanostructured thin film, which is thermally oxidized at 600° C. and under low oxygen partial pressures in the presence of a gaseous mixture of hydrogen gas and water vapor, wherein the water vapor is an overhead vapor of water at 20° C.
Figure 4C:
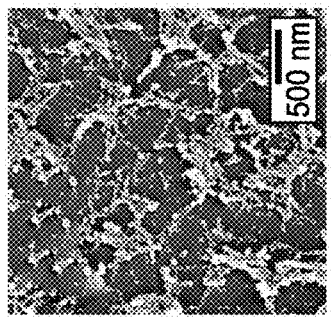
FIG. 4C is a SEM micrograph from a surface of the zinc oxide nanostructured thin film, which is thermally oxidized at 800° C. and under low oxygen partial pressures in the presence of a gaseous mixture of hydrogen gas and water vapor, wherein the water vapor is an overhead vapor of water at 20° C.
Figure 4D:
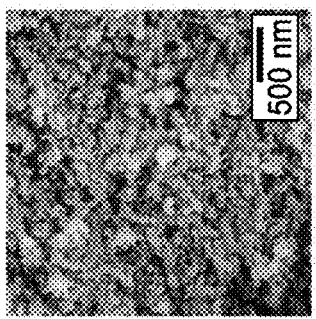
FIG. 4D is a SEM micrograph from a surface of the zinc oxide nanostructured thin film, which is thermally oxidized at 400° C. and in the presence of air.
Figure 4E:
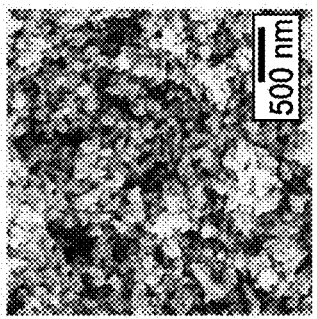
FIG. 4E is a SEM micrograph from a surface of the zinc oxide nanostructured thin film, which is thermally oxidized at 600° C. and in the presence of air.
Figure 4F:
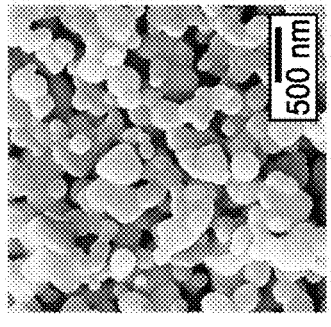
FIG. 4F is a SEM micrograph from a surface of the zinc oxide nanostructured thin film, which is thermally oxidized at 800° C. and in the presence of air.
Figure 4G:
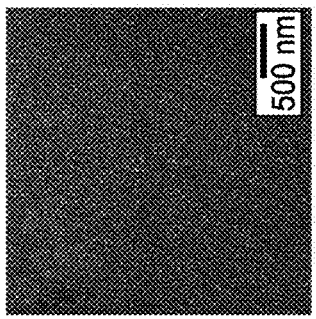
FIG. 4G is a SEM micrograph from a surface of the zinc oxide nanostructured thin film, which is fabricated by DC reactive sputtering followed by thermal oxidizing in argon at 400° C.
Figure 4H:
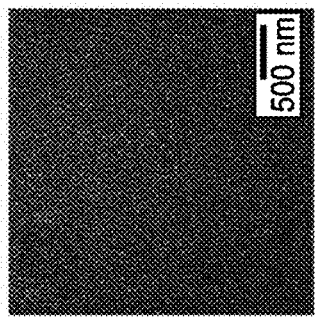
FIG. 4H is a SEM micrograph from a surface of the zinc oxide nanostructured thin film, which is fabricated by DC reactive sputtering followed by thermal oxidizing in argon at 400° C.
Figure 4I:
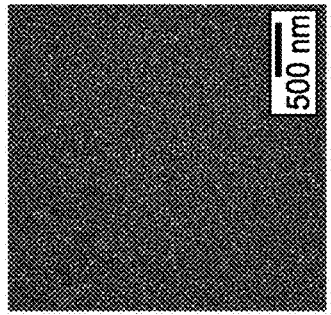
FIG. 4I is a SEM micrograph from a surface of the zinc oxide nanostructured thin film, which is fabricated by DC reactive sputtering followed by thermal oxidizing in argon at 400° C.

A further investigation on the morphologies of ZnO film obtained in oxidation of Zn in different annealing temperature under low oxygen partial pressure, in air and in DC sputtering has been carried out as shown in FIG. 4A-4I. In low oxygen partial pressure, the grain sizes and surface roughness was found to decrease in increasing annealing temperatures. In such case ZnO surface turned in to flakes at 400° C. temperature and then at 600° C. surface was covered with random aggregates of higher grain and porosity as shown in FIGS. 4A and 4B, respectively. At higher annealing temperature, such as 800° C., ZnO film turned into unpredicted morphology with reference to those obtained at lower annealing temperatures. While the ZnO films were obtained by thermal oxidation of sputtered Zn in air through annealing process, the morphologies were observed quite opposite to those obtained in low oxygen partial pressure. In such scenario, grain sizes were observed to increase at higher annealing temperatures. SEM micrographs of such films obtained at 400° C., 600° C. and 800° C. annealing temperatures are shown in FIGS. 4D, 4E, and 4F, respectively. ZnO films fabricated by one-step process, such as DC sputtering of Zn under oxygen chamber, might be very simple, but do to possess the prerequisites such as higher surface area and porosity. FIGS. 4G, 4H, and 4I show SEM micrographs of such films annealed at 400° C., 600° C. and 800° C. temperatures in argon, respectively. The film surfaces were observed to be smooth with reference to those obtained herewith.

EXAMPLE 5—STRUCTURAL ANALYSIS OF THE THIN FILM LAYER

The crystalline structure of the prepared films was examined by XRD analysis employing Shimadzu 6000 with Cu Kα irradiation at λ=1.5406 Å). The measured 2θ range was set to 20°-80° with a scan speed of 2°/min.

Figure 5A:
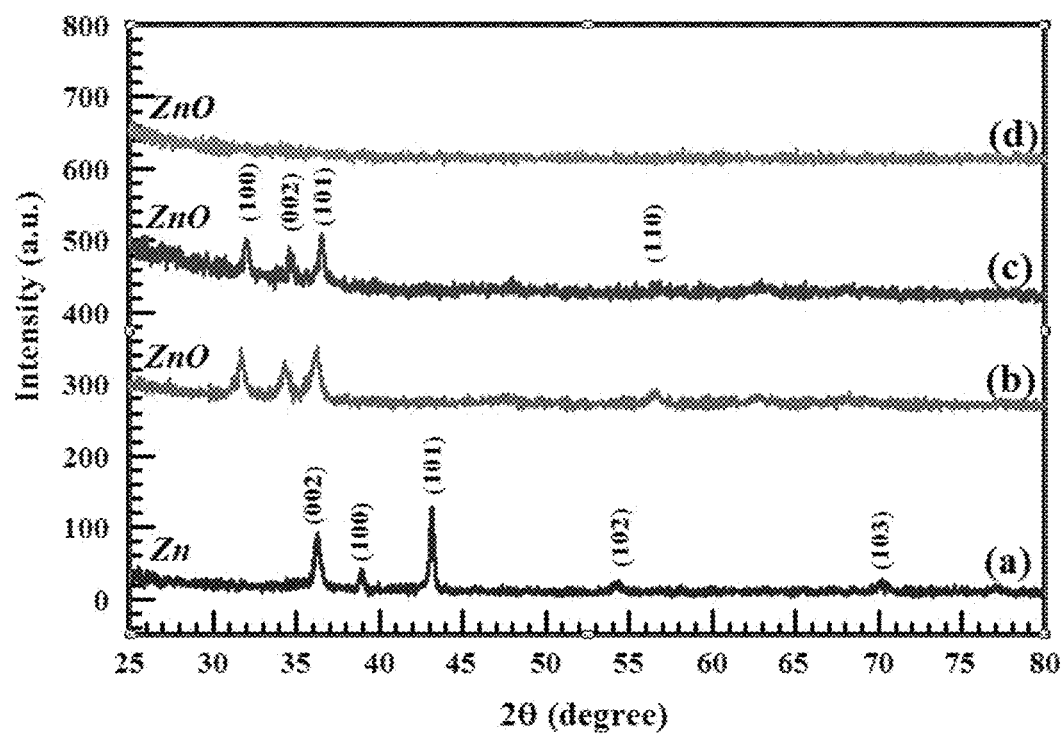
FIG. 5A represents (a) an XRD spectrum of zinc; and also XRD spectra of the zinc oxide nanostructured thin film, which is thermally oxidized at (b) 400° C., at (c) 600° C., and at (d) 800° C., under low oxygen partial pressures in the presence of a gaseous mixture of hydrogen gas and water vapor, wherein the water vapor is an overhead vapor of water at 20° C.

Structural analysis for as-fabricated Zn and ZnO films obtained in oxidation of Zn in different annealing temperature under low oxygen partial pressure, in air and in DC sputtering in argon has been carried thoroughly. The phase structure of the produced Zn and ZnO films was identified by XRD with Cu Kα incident radiation at 30 KV. FIG. 5A shows XRD patters of as-deposited Zn and ZnO films prepared by thermal oxidation of sputtered Zn films in low oxygen partial pressure at T*=20° C. and annealed at different temperatures for 2 h. As-deposited Zn confirmed several XRD peaks such as {002}, {100}, {101}, {102}, and {103} as shown in FIG. 5A(a). While such Zn was annealed at 400° C. and 600° C. temperatures, ZnO films with distinctive XRD pattern were obtained. At 400° C. temperature annealing, XRD peaks of {100}, {002}, {101}, and {110} were observed as shown in FIG. 5A(b). At higher temperature annealing such as 600° C., further XRD peaks, such as {102}, {103}, and {112} appeared in addition to enhanced aforementioned XRD patterns as shown in FIG. 5A(c). At 800° C. annealing, XRD pattern confirmed that the treated film was neither Zn nor ZnO film anymore as shown in FIG. 5A(d).

Figure 5B:
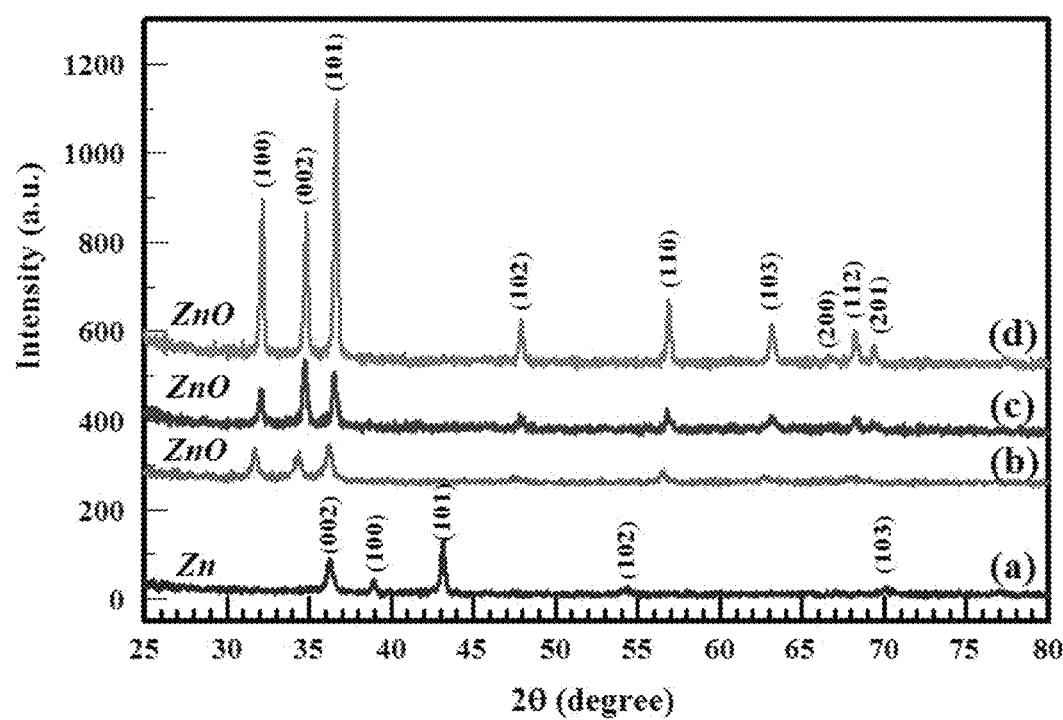
FIG. 5B represents (a) an XRD spectrum of zinc; and also XRD spectra of the zinc oxide nanostructured thin film, which is thermally oxidized in air at (b) 400° C., at (c) 600° C., and at (d) 800° C.
Figure 5C:
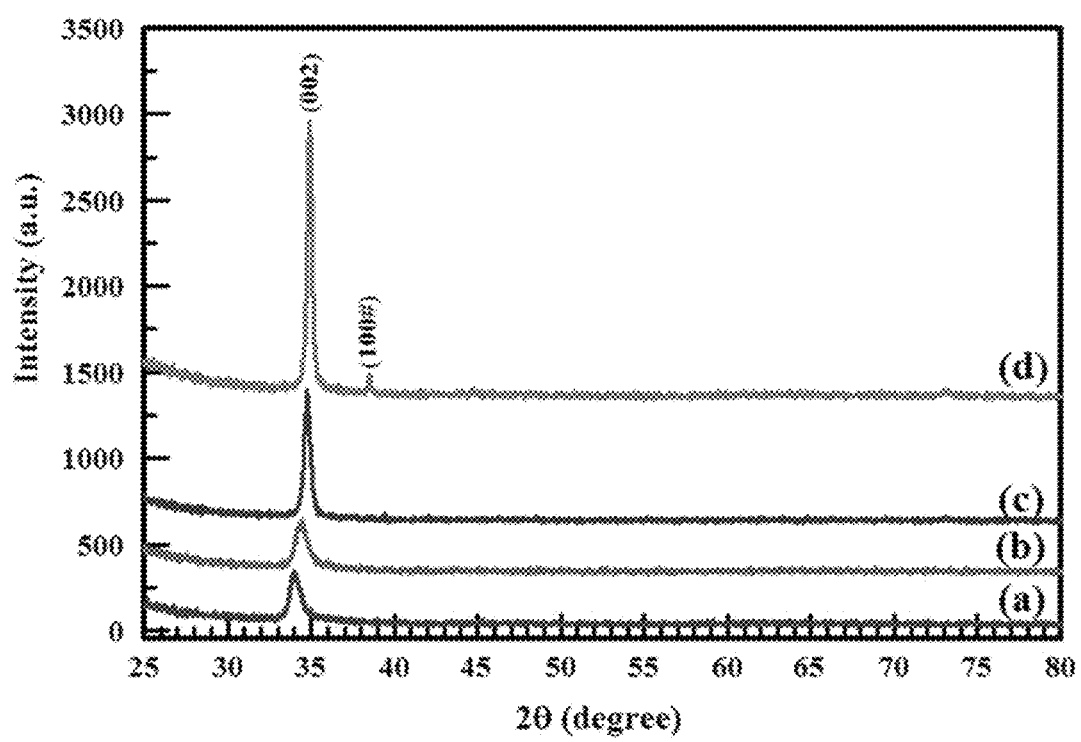
FIG. 5C represents (a) an XRD spectrum of zinc; and also XRD spectra of the zinc oxide nanostructured thin film, which is fabricated by DC reactive sputtering followed by thermal oxidizing in argon at (b) 400° C., at (c) 600° C., and at (d) 800° C.

FIG. 5B shows XRD patters of as-deposited Zn and ZnO films prepared by thermal oxidation of sputtered Zn films in air (i.e. $O_2$ environment) and annealed at different temperatures. Similar to those mentioned above, as-deposited Zn confirms several XRD peaks as shown in FIG. 5B(a). While such Zn is annealed at 400° C., 600° C. and 800° C. temperatures, ZnO films with distinctive XRD pattern were obtained similar to those observed above and as shown in FIGS. 5B(c) and 5B(d). As usual, XRD peak intensity got enhanced at increasing annealing temperatures. Peaks of the pattern coincide with those observed in standard ZnO (JCPDS S6-314). It is noteworthy that the diffraction peaks confirmed the growth of ZnO crystallites in different directions. No diffraction peaks from Zn or other impurities were found within the detection limit. XRD patterns of as-deposited ZnO by DC reactive sputtering, and further annealing at higher temperatures are shown in FIG. 5C. The results showed the presence of {002} diffraction peak only without and with annealing at different conditions highlighting a preferential orientation of the films along c-axis of the wurtzite structure of ZnO. After annealing, significant structural changes occurred. {002} peak was red shifted with increasing annealing temperatures. FIG. 5C(a-d) shows XRD patters of sputtered ZnO films without and with annealing temperatures of 400° C., 600° C. and 800° C. respectively.

EXAMPLE 6—COMPOSITIONAL ANALYSIS OF THE THIN FILM LAYER

The chemical analysis of the prepared samples was performed using XPS technique by an XPS apparatus Model: ESCALAB250Xi.

FIG. 6A-6F shows the XPS spectra of ZnO films prepared by oxidation of sputtered Zn at low oxygen partial pressure, ZnO oxidized in air, and ZnO prepared by DC reactive sputtering. The XPS survey spectra of the three samples (not shown here) contain only the constituent elements (Zn, O, and C). The detected carbon is attributed to the carbon adsorbed on the surface of the films during the exposure of the films to the ambient atmosphere. All binding energies were corrected for the charge shift using the C1s peak of graphitic carbon (BE=284.6 eV) as a reference.

Figure 6B:
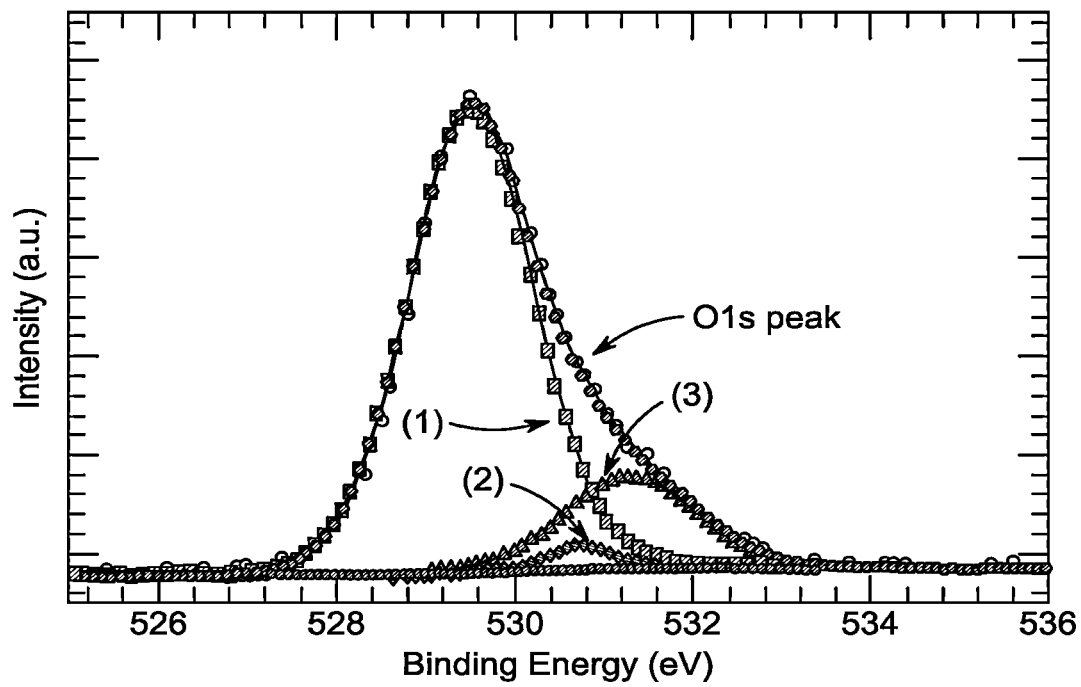
FIG. 6B represents a high resolution XPS spectrum of O1s peak of the zinc oxide nanostructured thin film, which is thermally oxidized at 600° C. in air.
Figure 6C:
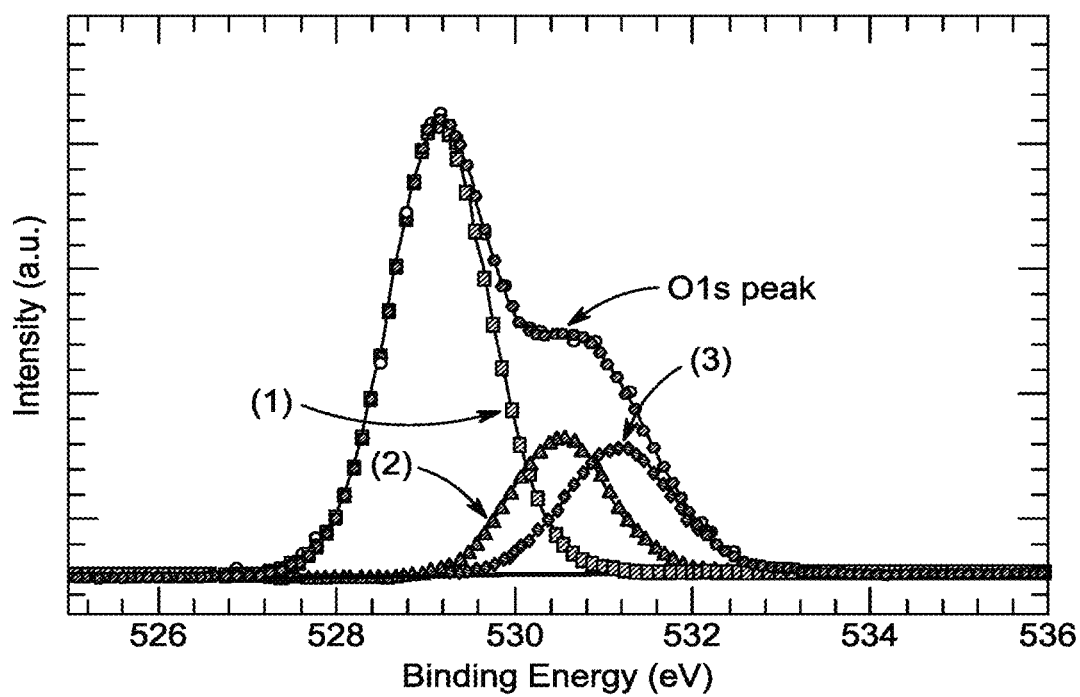
FIG. 6C represents a high resolution XPS spectrum of O1s peak of the zinc oxide nanostructured thin film, which is fabricated by DC reactive sputtering followed by thermal oxidizing in argon at 600° C.

The O1s peak in ZnO matrix is usually deconvoluted into three peaks representing three different environments: (1) $O^{2-}$ ions in the wurtzite ZnO structure at low binding energies (LBE), (2) oxygen vacancies at medium binding energies (MBE), and (3) $OH^-$ or any other surface adsorbed oxygen species at high binding energies (HBE). FIGS. 6A, 6B, and 6C display the XPS high resolution spectra of O1s spectra of ZnO films prepared by oxidation of sputtered Zn at low oxygen partial pressure, ZnO oxidized in air, and ZnO prepared by DC reactive sputtering, respectively. As can be seen, the three O1s peaks are clearly shown in all the samples. However, their weights differ from sample to another. The ratio of the weight of LBE ($O^{2-}$ ions) to MBE (oxygen vacancies) of the prepared samples of the ZnO films prepared by oxidation of sputtered Zn at low oxygen partial pressure, ZnO oxidized in air, and ZnO prepared by DC reactive sputtering were 0.72, 36.90 and 3.43 respectively. Thus, the ZnO film prepared by oxidized of sputtered Zn in $H_2/H_2O$ (low oxygen partial pressure) mixture has more oxygen vacancies compared with other two samples, which leads to the formation of more active sites on the surface for $H_2$ gas and could contribute to higher gas sensitivity.

Figure 6D:
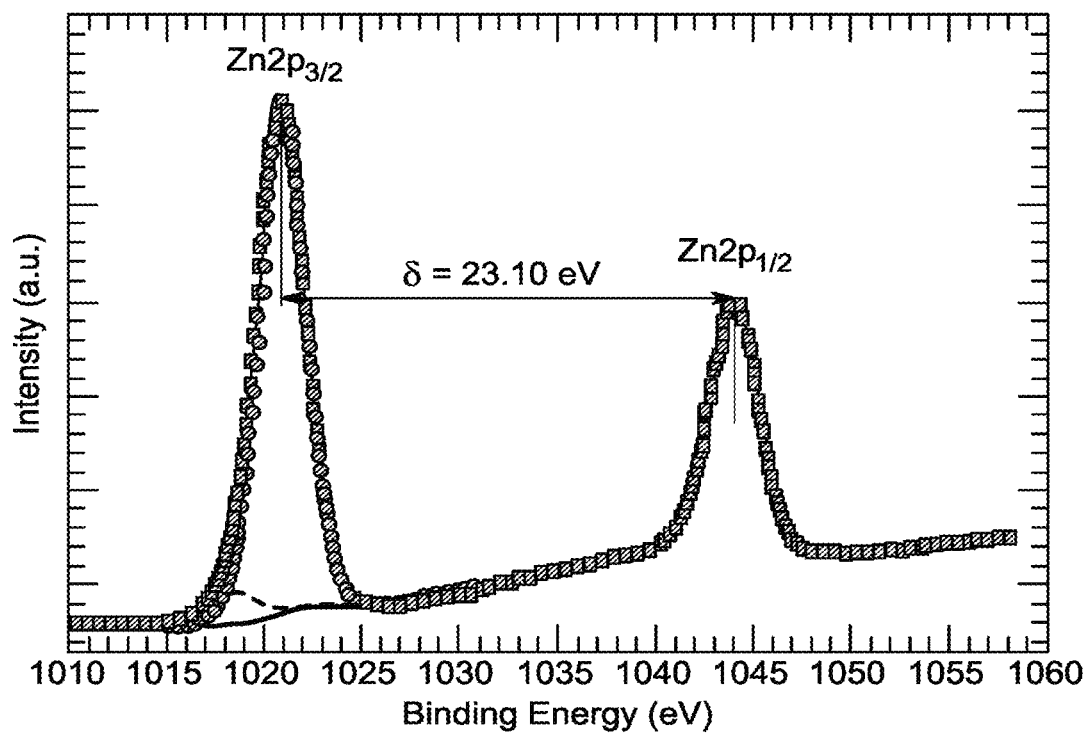
FIG. 6D represents a high resolution XPS spectrum of Zn2p peak of the zinc oxide nanostructured thin film, which is thermally oxidized at 600° C. under low oxygen partial pressures.
Figure 6E:
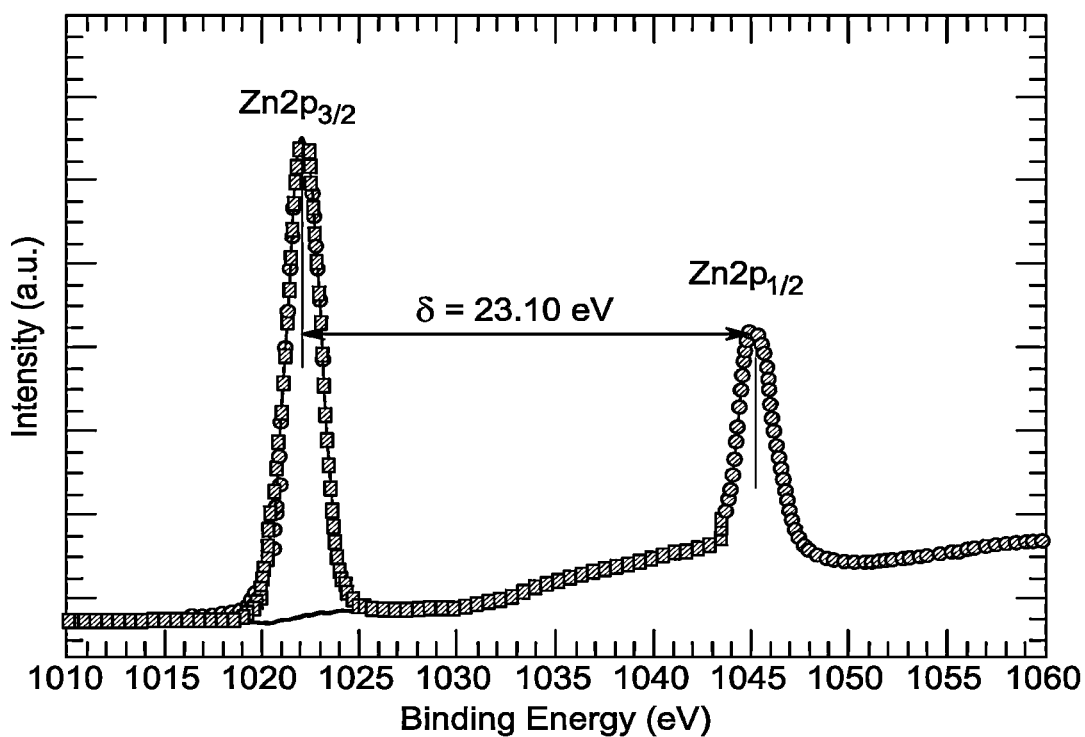
FIG. 6E represents a high resolution XPS spectrum of Zn2p peak of the zinc oxide nanostructured thin film, which is thermally oxidized at 600° C. in air.
Figure 6F:
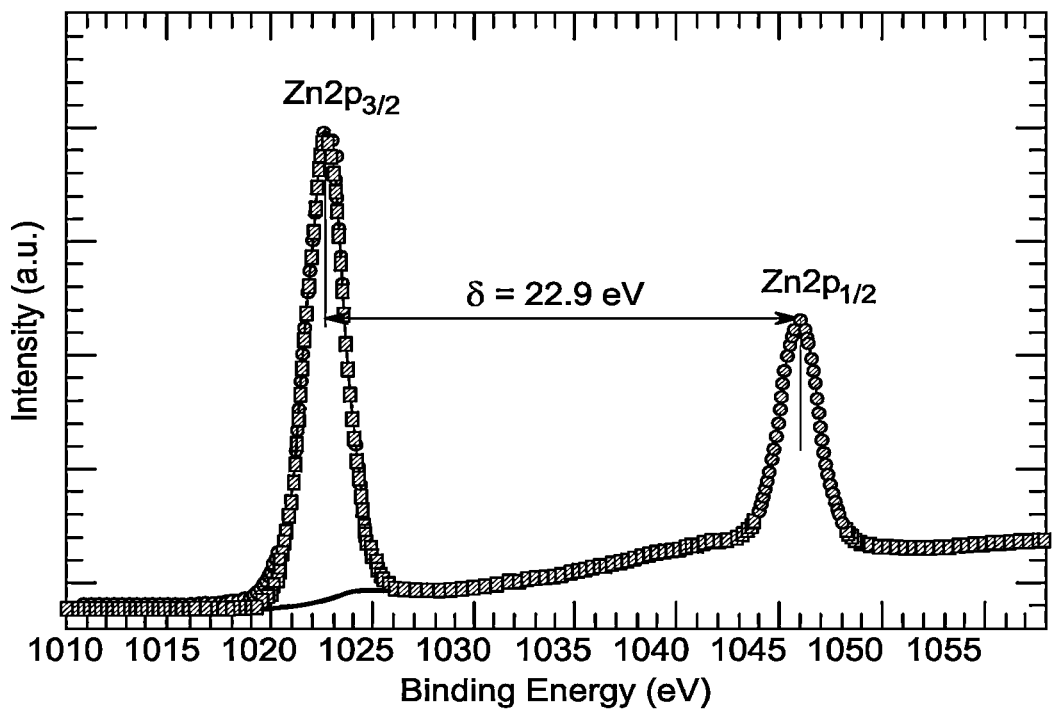
FIG. 6F represents a high resolution XPS spectrum of Zn2p peak of the zinc oxide nanostructured thin film, which is fabricated by DC reactive sputtering followed by thermal oxidizing in argon at 600° C.

FIGS. 6D, 6E, and 6F display the high-resolution Zn2p XPS spectra of the three samples. The Zn2p core-level spectrum is composed of $Zn2p_{3/2}$ and $Zn2p_{1/2}$ regions with separation distance (δ) close to 23 eV in all samples, which confirms the existence of Zn in $Zn^{2+}$ form. The binding energy of the $Zn2p_{3/2}$ spectra of ZnO films prepared by oxidation of sputtered Zn at low oxygen partial pressure, ZnO oxidized in air, and ZnO prepared by DC reactive sputtering centered at 1020.9 eV, 1022.2 and 1022.5 eV, respectively. As can be seen, the BE of the ZnO slightly shifted to lower binding energy compared with other two samples which can be ascribed by loss in the number of oxygen ions in the nanostructured ZnO. Such decreases in oxygen ions lead to reduce the charge transfer from Zn to $O_2$ and then increase the shielding effect of valence electron in the Zn ions. This shielding effect, reduction in the nuclear charge on the electron, decreases the binding energy of the core electrons in the Zn ions [C. Antoine, Vapor Pressure: A New relationship between pressure and temperature, Comptes Rendus, 107 (1888) 681-96, 836-37, 1888]. FIG. 6D also shows a small BE peak at 1018.3 eV which could be ascribed to the formation of Zn ions that are no longer coordinated with oxygen ions.

EXAMPLE 7—GAS SENSING PROPERTIES

FIG. 7 shows the response curve of the ZnO films prepared by thermal oxidation of sputtered Zn at low oxygen partial pressure ($H_2/H_2O$ at 600° C.). As observed, the resistance at all level of hydrogen (75, 150, 300, 600, 1200 ppm) at operating temperature 400° C. dropped upon exposure to $H_2$ gas. Alternatively, the resistance quickly increased to the base line resistance value when the $H_2$ gas was released from the chamber by the input of air. This tendency of the resistance was invariant, regardless of the type of the fabricated ZnO sensor. Different studies [Y. Y. Tay. S. Lib, Size dependence of Zn 2p3/2 binding energy in nanocrystalline ZnO, Applied Physics Letters, 88 (2006) 173118-173111; V. Galstyann, E. Comini, C. Baratto, G. Faglia, G. Sberveglieri, Nanostructured ZnO chemical gas sensors, Ceramics International, 41 (2015) 14239-14244; K. Vijayalakshmin, A. Renitta, Enhanced hydrogen sensing performance of tungsten activated ZnO nanorod arrays prepared on conductive ITO substrate, Ceramics International, 41 (2015) 14315-14325; O. Lupan, L. Chow, Th. Pauporté, L. K. Ono, B. Roldan Cuenya, G. Chai, Highly sensitive and selective hydrogen single-nanowire nanosensor, Sensors and Actuators B, 173 (2012) 772-780] suggested that the decrease/increase in resistance value of the ZnO film in the presence/absence of $H_2$ could be explained as follows: when the ZnO layer is exposed to air atmosphere, the ambient oxygen molecules adsorbed on ZnO surface capture electron from the ZnO conduction band, leading to produce oxygen ions ($O_2^-$ at room temperature, $O^-$ between 100 and 300° C., $O^{2-}$ above 300° C.). As a result, the density of electrons in the conduction band of ZnO sensor decreases and a space charge region which serves as a potential barrier for electron transfer is formed on the surface of the ZnO, causing in high air resistance. When the ZnO films are exposed to hydrogen, the adsorbed oxygen ions on the surface are desorbed, and the electron that previously trapped are released back into the conduction band, leading to an increase in the electron concentration in the conduction band of the ZnO, decreasing the electrical resistance of the sensor.

Figure 9:
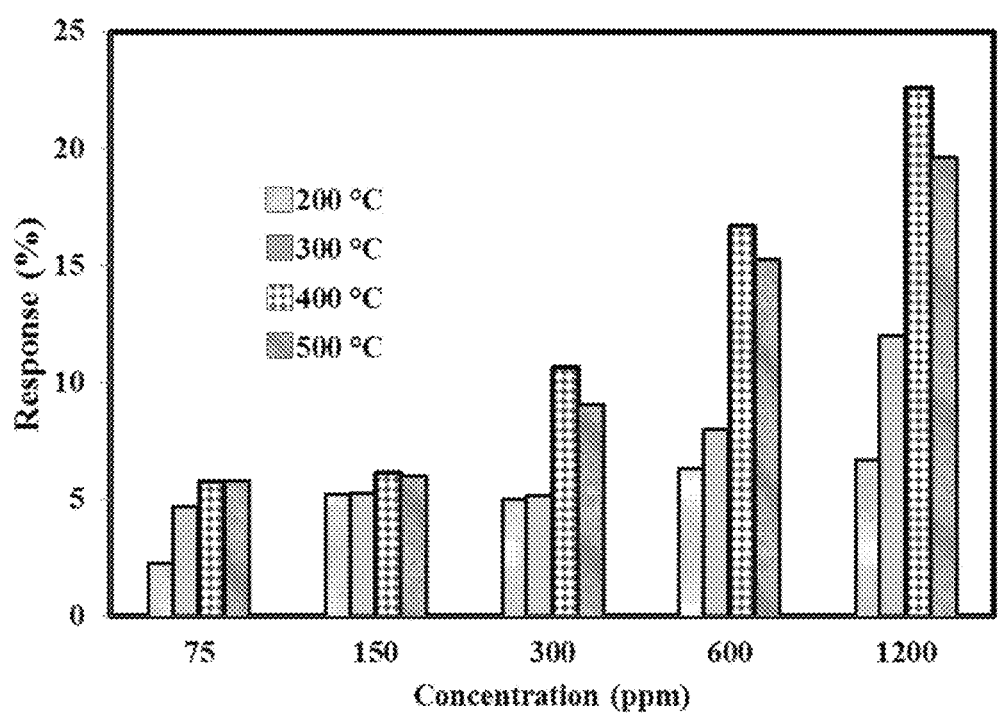
FIG. 9 represents values of the response factor of the hydrogen gas sensor when subjected to a fluid stream with different concentrations of hydrogen gas at various temperatures, wherein the hydrogen gas sensor is fabricated by thermal oxidation of zinc under low oxygen partial pressures at 600° C.

Repeatability or reproducibility, which is defined as the deviation in measurements obtained several times via the gas sensor under the same operating temperature conditions over a period, is another important parameter of the sensor characteristic. FIG. 8 shows decent response repeatability over four consecutive cycles of exposure to 600 ppm $H_2$ at an operating temperature of 400° C. Results displayed that the response of the film was almost constant and the standard deviation of the response was less than 1% confirming the good reproducibility of sensor material. FIG. 9 displays the response of ZnO sensor oxidized at 600° C. in low oxygen partial pressure upon exposure to 75, 150, 300, 600 and 1200 ppm of $H_2$ diluted in dry air at different operating temperatures (200-500° C.). As can be observed, the optimal working temperature for achieving the maximum hydrogen response are obtained at 400° C., which is similar to ZnO thin films catalyzed by gold nanoparticles prepared by DC sputtering followed by furthered heat-treatment in Ar [Q. A. Drmosh, Z. H. Yamani, Synthesis, characterization, and hydrogen gas sensing properties of AuNs-catalyzed ZnO sputtered thin films, Applied Surface Science, 375 (2016) 57-64].

Figure 10:
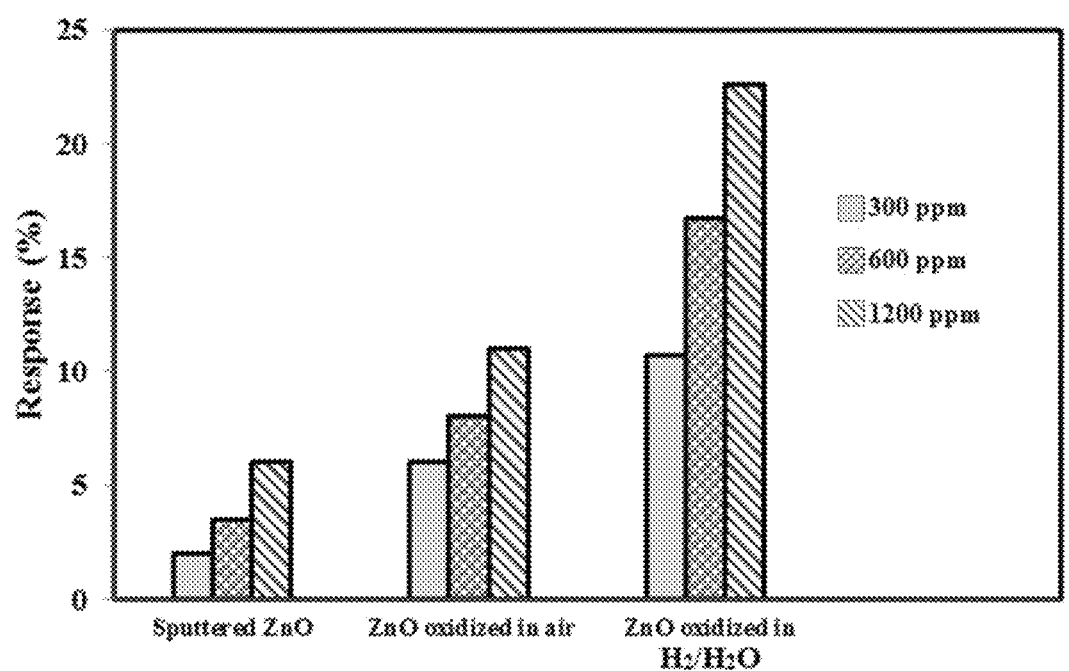
FIG. 10 represents values of the response factor of the hydrogen gas sensor when subjected to a fluid stream with different concentrations of hydrogen gas at 400° C., wherein the hydrogen gas sensor is fabricated by DC reactive sputtering followed by thermal oxidation in argon at 600° C.; by thermal oxidation of zinc in air at 600° C.; and by thermal oxidation of zinc under low oxygen partial pressures at 600° C.

To evaluate the performance of the gas sensors fabricated by our method, the gas sensing characteristics (response and response time) were compared with ZnO films prepared by sputtering technique by means of two different ways. FIG. 10 shows the response of three different ZnO sensors: (1) sputtered ZnO, (2) ZnO prepared by thermal oxidized sputtered Zn in air, and (3) ZnO fabricated by oxidized sputtered Zn in $H_2/H_2O$ mixture at three different concentrations (300, 600, 1200 ppm) at 400° C. as an operating temperature. As can be seen, the ZnO sensors fabricated at low oxygen partial pressure ($H_2/H_2O$ mixture) exhibited much higher response compared with other two ZnO sensors at all hydrogen levels. For example, at a concentration of 600 ppm, the response value of ZnO films oxidized at very low oxygen partial pressure is about 16.1%, whereas it is about 3.8% and 7.8% for ZnO films prepared by DC reactive sputtering and oxidized sputtered Zn in air, and ZnO prepared by respectively.

FIG. 11 shows the response speed or response time (the times to reach 90% variation in resistance upon exposure to hydrogen) of the ZnO films prepared by oxidized at low oxygen partial pressure and other sensors towards different concentrations of hydrogen gas (300, 600, 1200 ppm) at 400° C. As can be seen, the response time values of the developed ZnO film are significantly shorter compared to other two sensors. For instance, a five and four times faster response was obtained for a ZnO film prepared at low oxygen partial pressure compared with sputtered ZnO and ZnO oxidized in air respectively.

For the compact ZnO film that prepared by DC reactive sputtering, it is theoretically hard for hydrogen molecules to diffuse into the interior of sensing material, therefore sensing reactions between adsorbed oxygen ions and hydrogen gas can only occur on the outer surface of the film and result in only one flat depletion region. For ZnO film prepared by oxidized of sputtered Zn in air, unlike to the tightly compact sputtered ZnO film, the outer surface was rough with some pores that enhanced the response of the sensor. In case of ZnO film prepared at low oxygen partial pressure, numerous pores serving as hydrogen diffusion channels were formed on the ZnO surface. This highly porous nature on the ZnO surface provides more active sites and allows of formation of electron depletion region on both the outer and inner ZnO surfaces.

Figure 13:
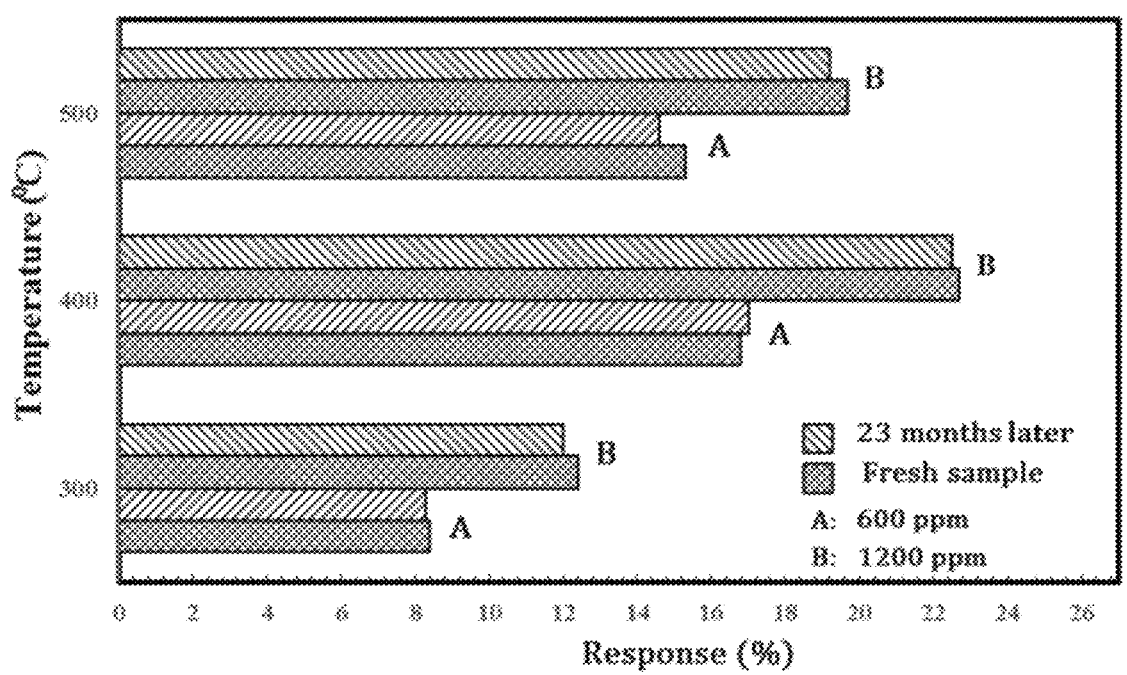
FIG. 13 represents values of the response factor of the hydrogen gas sensor when subjected to a fluid stream with different concentrations of hydrogen gas at various temperatures, wherein the hydrogen gas sensor is fabricated by thermal oxidation of zinc under low oxygen partial pressures at 600° C., wherein the hydrogen gas sensor is used as-fabricated; the hydrogen gas sensor is used 23 months after fabrication.

To study the selective $H_2$-sensing capability of the fabricated sensor, the responses to other gases were examined. FIG. 12 illustrates the selectivity of the sensors to different gases, such as 10,000 ppm $CO_2$, 400 ppm $NH_3$, and 10,000 ppm $C_5H_{10}$ at working temperatures of 400° C. The $CO_2$ and $C_5H_{10}$ gases were tested at relatively high concentrations because their responses were negligible at the low concentration of 1000 ppm. As can be seen, the fabricated sensor was almost insensitive to $CO_2$ and $C_5H_{10}$ even at very high concentrations confirming an excellent selectivity towards $H_2$. Long term stability of the sensor devices is another important aspect in the evaluation of their suitability. To investigate the long-term stability of ZnO sensor prepared by thermal oxidation of metallic Zn at low oxygen partial pressure, the gas sensing characteristic was evaluated once again after twenty-three months. FIG. 13 shows the gas sensing response to 600 ppm and 1200 ppm $H_2$ at 300° C., 400° C., and 500° C. of fresh sample and after 23 months. It can be clearly seen that the response of the fabricated sensor was stable within a range of 1% confirming the high long term stability of the prepared sensor. In addition, it was found that the base resistance of the sensor was increased about 18% which could be attributed to a reduced concentration of oxygen vacancies within the ZnO lattice with time.

The gas sensing performance of the ZnO sensor prepared by this method is compared with the previously reported sputtered metal oxides $H_2$ gas sensors, as displayed in Table 1. It can be observed that the ZnO sensor prepared by this method showed good response. As the response time, our proposed ZnO sensor takes great advantages when compared with other sputtered metal oxides sensor except with ref [Y. Choi, S. Hong, $H_2$ sensing properties in highly oriented $SnO_2$ thin films, Sensors and Actuators B, 125 (2007) 504-509] used 10,000 ppm of $H_2$ at 550° C. It is worthy to emphasize that the response time of our sensor listed in the Table 1 was acquired for 1200 ppm $H_2$ at 400° C., which can be greatly improved with the same concentration and operating temperature in ref [Y. Choi, S. Hong, $H_2$ sensing properties in highly oriented $SnO_2$ thin films, Sensors and Actuators B, 125 (2007) 504-509]. It is also observed that the proposed ZnO sensor long term stability, which is, to the best of our knowledge, has the highest long term stability ever reported.

TABLE 1

ZnO sensors prepared by thermal oxidation of sputtered Zn at low $PO_2$ in comparison with the metal oxide sensors prepared by sputtering technique in literature.

| Materials | Preparation method | Optimum Temp. (° C.) | Maximum response (S) | Conc. (ppm) | Response time (sec.) | Selectivity | Long term stability | Ref. |
|---|---|---|---|---|---|---|---|---|
| ZnO | RF reactive sputtering | 400 | 2.3[(1)] | 100 | <20 min. | Not reported | Not reported | Y. Liu, C. Gao, X. Pan, Y. Xie, M. Zhou, J. Song, H. Zhang, Z. Liu, Q. Zhao, Y. Zhang, E. Xie, Synthesis and $H_2$ sensing properties of aligned ZnO nanotubes, Applied Surface Science, 257 (2011) 2264-2268. |

TABLE 1-continued

ZnO sensors prepared by thermal oxidation of sputtered Zn at low $PO_2$ in comparison with the metal oxide sensors prepared by sputtering technique in literature.

| Materials | Preparation method | Optimum Temp. (° C.) | Maximum response (S) | Conc. (ppm) | Response time (sec.) | Selectivity | Long term stability | Ref. |
|---|---|---|---|---|---|---|---|---|
| $SnO_2$ | RF sputtering | 550 | 300[1] | 10,000 | 16 s | Good selectivity with CO | Not reported | Y. Choi, S. Hong, $H_2$ sensing properties in highly oriented $SnO_2$ thin films, Sensors and Actuators B, 125 (2007) 504-509. |
| CuO | Cu films fabricated by Ion beam sputtering followed by heat-treatment in air | 350 | 1.1[2] | 1,000 | 10 to 15 min. | Not reported | Not reported | H. Steinebach, S. Kannan, L. Riethb, F. Solzbacher, Thin copper oxide films prepared by ion beam sputtering with subsequent thermal oxidation: Application in chemiresistors, Applied Surface Science, 389 (2016) 751-759. |
| NiO | RF sputtering followed heat-treatment in air at 900° .C | 600 | 55[3] | 5,000 | 9 min. | high selectivity with CO2 and $NH_3$ | Not reported | H. Steinebach, S. Kannanb, L. Rieth, F. Solzbacher, H2 gas sensor performance of NiO at high temperatures in gas mixtures, Sensors and Actuators B, 151 (2010) 162-168. |
| ITO | RF magnetron sputtering at 648K | 127 | 1.6[4] | 1,000 | Not reported | Not reported | Not reported | V. VasanthiPillay, K. Vijayalakshmi, Effect of rf power on the structural properties of indium tin oxide thin film prepared for application in hydrogen gas sensor, J Mater Sci: Mater Electron, 24 (2013) 1895-1899. |
| ZnO | RF sputtering | 250 | 2250[1] (static response) | 200 | ≈5 min | Not reported | Not reported | H. S. Al-Salmana,, M.J. Abdullah, Hydrogen gas sensing based on ZnO nanostructure prepared by RF-sputtering on quartz and PET substrates, Sensors and Actuators B, 181 (2013) 259-266. |
| Porous sputtered ZnO | The method of the present disclosure | 400° C. | 23[5] | 1,200 | 110 s. | High selectivity with $CO_2$, $C_5H_{10}$, and good selectivity with $NH_3$ | High | The present disclosure. |

[1] $S = R_a/R_g$; [2] $S = (Z_a - Z_g)/Z_a$; [3] $S = (R_a - R_g)/R_a$; [4] $S = (R_a - R_g)/R_g$; [5] $S = [(R_a - R_g)*100]/R_a$, where $R_g$, $R_a$, $Z_a$, and $Z_g$ are tie electrical resistances of the sensor in the presence of hydrogen, the electrical resistant zes of the sensor in air, the real part of the impedance for dry air atmosphere and the r eal part of the impedance for the hydrogen atmosphere, respectively.

A ZnO nanostructured thin film is fabricated by thermal oxidation of metallic Zn at ultra-low values of oxygen partial pressure, with substantially improved surface roughness and porosity that facilitated better gas sensing performance toward low levels of $H_2$ (75-1200 ppm). The low oxygen partial pressure was obtained by a proper mixing of hydrogen gas and water vapor. As obtained low oxygen partial pressure was fed to the closed chamber to oxidize sputtered Zn films at different annealing temperatures (400-800° C.). The morphological, structural, compositional, and sensing properties of the prepared films were investigated using different analytical techniques. Microstructural analysis of the ZnO films fabricated at different values of oxygen partial pressure displayed significantly improved surface roughness and variations in porosity with reference to those obtained by oxidation of sputtered Zn film in air and sputtered ZnO in argon. Phase structures of as-fabricated ZnO nanostructures were identified by distinctive XRD patterns. The peaks were enhanced at higher annealing temperatures. Peaks of the pattern coincide with those observed in standard ZnO (JCPDS S6-314). It is noteworthy that the diffraction peaks confirmed the growth of ZnO crystallites in different directions. No diffraction peaks from Zn or other impurities were found within the detection limit. ZnO film fabricated by thermal oxidized of sputtered Zn in low oxygen partial pressure possessed more oxygen vacancies that lead to the formation of more active sites to target gas to be efficient gas sensor. The sensing test results showed that the ZnO thin films prepared at low oxygen partial pressure have higher sensitivity and faster response toward hydrogen.

Thus, the foregoing discussion discloses and describes merely exemplary embodiments of the present invention. As will be understood by those skilled in the art, the present invention may be embodied in other specific forms without departing from the spirit or essential characteristics thereof. Accordingly, the disclosure of the present invention is intended to be illustrative, but not limiting of the scope of the invention, as well as other claims. The disclosure, including any readily discernible variants of the teachings herein, defines, in part, the scope of the foregoing claim terminology such that no inventive subject matter is dedicated to the public.

The invention claimed is:

1. A method of fabricating a gas sensor that comprises a metal oxide nanostructured thin film deposited on a substrate, the method comprising:
   depositing a metal thin film on the substrate; and
   thermally oxidizing the metal thin film at a temperature of 200 to 1,000° C. in the presence of a gaseous mixture with an oxygen partial pressure in the range of $10^{-60}$ to $10^{-1}$ atm to form the metal oxide nanostructured thin film on the substrate, thereby fabricating the gas sensor;
   wherein the metal is Zn and the metal oxide nanostructured thin film is a zinc oxide nanostructured thin film; and
   wherein the zinc oxide nanostructured thin film is porous having first pores with an average pore size of 1 to 20 nm and second pores with an average pore size of 4 to 12 Å.

2. The method of claim 1, wherein the zinc oxide nanostructured thin film has a thickness in the range of 10 to 1,000 nm.

3. The method of claim 1, wherein the substrate is a glass substrate or a silicon wafer substrate.

4. The method of claim 1, wherein the zinc oxide nanostructured thin film has a lattice structure with a weight ratio of low binding energy $O^{2-}$ ions to medium binding energy oxygen vacancies in a range of 0.1 to 1.0.

5. The method of claim 1, wherein the gas sensor is a hydrogen gas sensor.

6. The method of claim 5, wherein a temperature of the gaseous mixture is in the range of 10 to 100° C. before the thermally oxidizing.

7. The method of claim 5, wherein a temperature of the gaseous mixture is in the range of 80 to 100° C. before the thermally oxidizing, and
   wherein the zinc oxide nanostructured thin film has a sheet-like morphology.

8. The method of claim 5, wherein the gaseous mixture comprises hydrogen gas and water vapor.

9. The method of claim 8, wherein a ratio of a partial pressure of hydrogen gas to a partial pressure of water vapor in the gaseous mixture is in the range of 1:100 to 1:2000, and
   wherein the gaseous mixture has an oxygen partial pressure in the range of $10^{-20}$ to $10^{-15}$ atm.

10. The method of claim 8, wherein the metal thin film is thermally oxidized in the presence of the gaseous mixture for 2 to 6 hours.

* * * * *